(12) United States Patent
Kubo

(10) Patent No.: US 11,213,214 B2
(45) Date of Patent: Jan. 4, 2022

(54) ELECTRONIC BLOOD PRESSURE MONITOR

(71) Applicant: OMRON HEALTHCARE CO., LTD., Muko (JP)

(72) Inventor: Takeshi Kubo, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 283 days.

(21) Appl. No.: 16/015,257

(22) Filed: Jun. 22, 2018

(65) Prior Publication Data

US 2018/0296101 A1 Oct. 18, 2018

Related U.S. Application Data

(63) Continuation of application No. PCT/JP2016/079314, filed on Oct. 3, 2016.

(30) Foreign Application Priority Data

Dec. 28, 2015 (JP) .............................. JP2015-257066

(51) Int. Cl.
*A61B 5/0225* (2006.01)
*A61B 5/022* (2006.01)
(Continued)

(52) U.S. Cl.
CPC ............ *A61B 5/0225* (2013.01); *A61B 5/022* (2013.01); *A61B 5/02108* (2013.01);
(Continued)

(58) Field of Classification Search
None
See application file for complete search history.

(56) References Cited

U.S. PATENT DOCUMENTS 6,224,558 B1 * 5/2001 Clemmons ......... A61B 5/02233
600/490
2004/0077958 A1 4/2004 Kato et al.
(Continued)

FOREIGN PATENT DOCUMENTS

CN 1400882 A 3/2003
CN 1517060 A 8/2004
(Continued)

OTHER PUBLICATIONS

English translation of Official Communication issued in International Patent Application No. PCT/JP2016/079314, dated Jun. 28, 2018.

(Continued)

*Primary Examiner* — Etsub D Berhanu
*Assistant Examiner* — Aurelie H Tu
(74) *Attorney, Agent, or Firm* — Keating and Bennett, LLP

(57) ABSTRACT

An electronic blood pressure monitor of the present invention includes a blood pressure measurement cuff that is to be worn on a measurement site of a measurement subject. The electronic blood pressure monitor includes a blood pressure measurement unit that measures a blood pressure value of the measurement subject using the cuff. The electronic blood pressure monitor includes an external compression detection unit that detects whether or not there was external compression on the cuff during blood pressure measurement performed by the blood pressure measurement unit.

5 Claims, 25 Drawing Sheets

(51) Int. Cl.
 *A61B 5/021* (2006.01)
 *A61B 5/11* (2006.01)
 *A61B 5/00* (2006.01)
(52) U.S. Cl.
 CPC ........... *A61B 5/1116* (2013.01); *A61B 5/4806* (2013.01); *A61B 5/7221* (2013.01); *A61B 2560/0475* (2013.01)

(56) References Cited

U.S. PATENT DOCUMENTS

| | | | |
|---|---|---|---|
| 2004/0254484 | A1 | 12/2004 | Hashimoto et al. |
| 2009/0163823 | A1* | 6/2009 | Takahashi ............ A61B 5/6843 600/490 |
| 2009/0312651 | A1 | 12/2009 | Sano et al. |
| 2010/0305459 | A1* | 12/2010 | Whitt .................. A61B 5/0295 600/490 |
| 2013/0226010 | A1 | 8/2013 | Hotta |
| 2014/0200413 | A1 | 7/2014 | Hotta |
| 2014/0257116 | A1* | 9/2014 | Kobayashi ......... A61B 5/02225 600/490 |
| 2014/0276144 | A1* | 9/2014 | Whitt ................. A61B 5/02007 600/490 |
| 2017/0238824 | A1* | 8/2017 | Woerlee ................. A61B 5/022 |
| 2018/0263517 | A1* | 9/2018 | Kubo .................... A61B 5/022 |

FOREIGN PATENT DOCUMENTS

| | | |
|---|---|---|
| CN | 101340845 A | 1/2009 |
| CN | 202723842 U | 2/2013 |
| CN | 103919526 A | 7/2014 |
| CN | 104605834 A | 5/2015 |
| JP | 57-173038 A | 10/1982 |
| JP | 60-225538 A | 11/1985 |
| JP | 2-82940 A | 3/1990 |
| JP | 05-176900 A | 7/1993 |
| JP | 2008-188197 A | 8/2008 |
| JP | 2012-061105 A | 3/2012 |
| JP | 2013-198720 A | 10/2013 |
| JP | 2014-133049 A | 7/2014 |
| JP | 2014-233529 A | 12/2014 |
| WO | 2006/124768 A1 | 11/2006 |

OTHER PUBLICATIONS

Official Communication issued in corresponding Chinese Patent Application No. 201680076489.8, dated May 21, 2020.
Official Communication issued in International Patent Application No. PCT/JP2016/079314, dated Dec. 6, 2016.

* cited by examiner

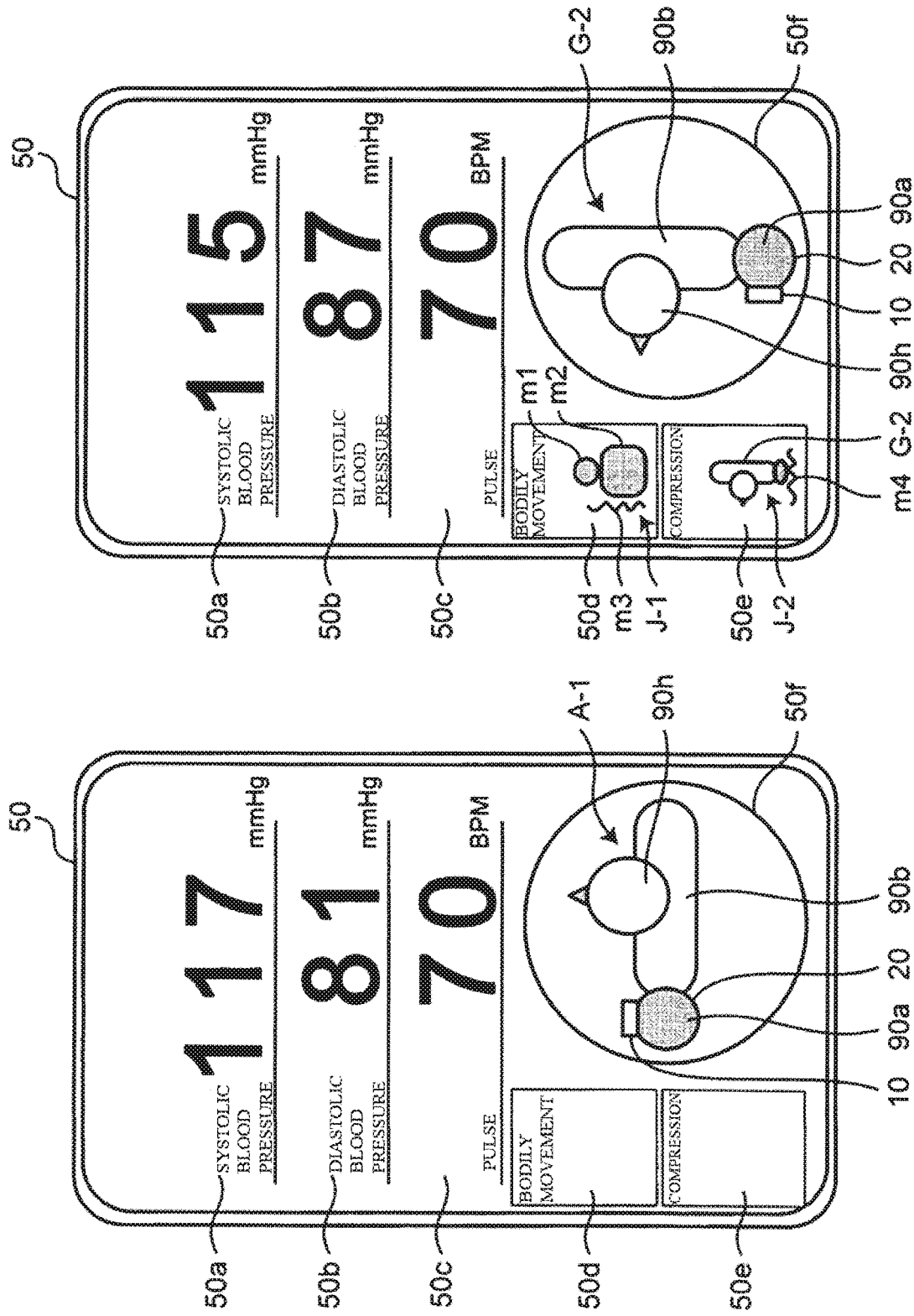

ELECTRONIC BLOOD PRESSURE MONITOR

CROSS-REFERENCE TO RELATED APPLICATIONS

This is a continuation application of International Application No. PCT/JP2016/079314, with an International filing date of Oct. 3, 2016, which claims priority of Japanese Patent Application No. 2015-257066 filed on Dec. 28, 2015, the entire content of which is hereby incorporated by reference.

TECHNICAL FIELD

The present invention relates to an electronic blood pressure monitor, and more specifically relates to an electronic blood pressure monitor that includes a cuff worn on a measurement site of a measurement subject, and that increases the pressure of the cuff by supplying a fluid thereto to compress the measurement site and perform blood pressure measurement.

BACKGROUND ART

Conventionally, as this type of electronic blood pressure monitor, as disclosed in Patent Document 1 (JP 2008-188197A) for example, an electronic blood pressure monitor is known in which, upon being started up, air is supplied to a cuff, pressure increase is started, and based on the extent of the increase in the pressure in the cuff, it is determined whether or not the cuff is being worn appropriately on a measurement site such as an upper arm.

SUMMARY OF INVENTION

Incidentally, in recent years, the importance of measuring night-time blood pressure for treatment of hypertension has been receiving attention. In night-time blood pressure measurement, blood pressure measurement is generally performed automatically using a timer setting during a sleep period of the measurement subject, and therefore the measurement subject cannot consciously correct his or her orientation during blood pressure measurement. For this reason, blood pressure values obtained in various orientations can be recorded. For example, if the measurement subject, who is lying on a bed surface, places the cuff, which is worn on the upper arm (measurement site), under his or her torso, the cuff will be compressed from the outside (the torso and the bed surface), and therefore there is a possibility that the recorded blood pressure value will be influenced. Accordingly, it is convenient if a user (includes a medical professional such as a doctor or a nurse, for example, in addition to the measurement subject; the same applies in the following description) can later check whether or not there was compression from the outside (external compression) on the cuff during blood pressure measurement.

However, as far as the applicants of the present application know, an electronic blood pressure monitor according to which a user can check whether or not there was external compression on a cuff during blood pressure measurement has not conventionally existed.

In view of this, the present invention aims to provide a blood pressure monitor according to which a user can check whether or not there was external compression on the cuff during blood pressure measurement.

In order to solve the above-described problem, the electronic blood pressure monitor of this disclosure includes:

a blood pressure measurement cuff configured to be worn on a measurement site of a measurement subject;

a blood pressure measurement unit configured to measure a blood pressure value of the measurement subject using the cuff; and an external compression detection unit configured to detect whether or not there was external compression on the cuff during the blood pressure measurement performed by the blood pressure measurement unit, wherein in each predetermined pressure segment, the external compression detection unit calculates a cuff compliance, which is an amount of air that is to be pumped into the cuff and is needed to increase pressure in the cuff per unit pressure, as the pressure of the cuff is increased by the blood pressure measurement unit during blood pressure measurement, and the external compression detection unit determines whether or not there is external compression on the cuff based on a change indicated by the cuff compliance in each pressure segment.

In the present specification, "during blood pressure measurement" does not indicate the entire period in which the blood pressure measurement cuff is worn for night-time blood pressure measurement and the like, for example, but indicates a timing during which the blood pressure values of the measurement subject are measured by actually increasing or reducing the pressure of the above-described blood pressure measurement cuff.

Also, "external compression" indicates compression from the outside of the external circumferential surface of the blood pressure monitor that is wrapped around the measurement site. In other words, "external compression" does not encompass compression from the measurement site (inner circumferential surface side of the cuff) around which the blood pressure measurement cuff is wrapped. Typically, external compression occurs when the measurement subject lying on the bed surface places the cuff worn on the measurement site under the torso in the case of night-time blood pressure measurement. Note that "bed surface" widely indicates a surface on which a measurement subject can lie, such as an upper surface of a bed or futon. The torso of the measurement subject may be wearing clothes.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 8A is a diagram showing a correspondence relationship between the orientation (torso angle and arm position) of the measurement subject during blood pressure measurement and the outputs (XZ coordinates and XY coordinates) of the acceleration sensor.

FIG. 8B is a diagram showing a correspondence relationship between the orientation (torso angle and arm position) of the measurement subject during blood pressure measurement and the outputs (XZ coordinates and XY coordinates) of the acceleration sensor.

FIG. 8C is a diagram showing a correspondence relationship between the orientation (torso angle and arm position) of the measurement subject during blood pressure measurement and the outputs (XZ coordinates and XY coordinates) of the acceleration sensor.

FIG. 8D is a diagram showing a correspondence relationship between the orientation (torso angle and arm position) of the measurement subject during blood pressure measurement and the outputs (XZ coordinates and XY coordinates) of the acceleration sensor.

FIG. 8E is a diagram showing a correspondence relationship between the orientation (torso angle and arm position) of the measurement subject during blood pressure measurement and the outputs (XZ coordinates and XY coordinates) of the acceleration sensor.

FIG. 8G is a diagram showing a correspondence relationship between the orientation (torso angle and arm position) of the measurement subject during blood pressure measurement and the outputs (XZ coordinates and XY coordinates) of the acceleration sensor.

FIG. 8H is a diagram showing a correspondence relationship between the orientation (torso angle and arm position) of the measurement subject during blood pressure measurement and the outputs (XZ coordinates and XY coordinates) of the acceleration sensor.

FIGS. 9A and 9B are diagrams illustrating images to be displayed on a display device of the blood pressure monitor.

DESCRIPTION OF EMBODIMENTS

Configuration of Blood Pressure Monitor

Figure 1:
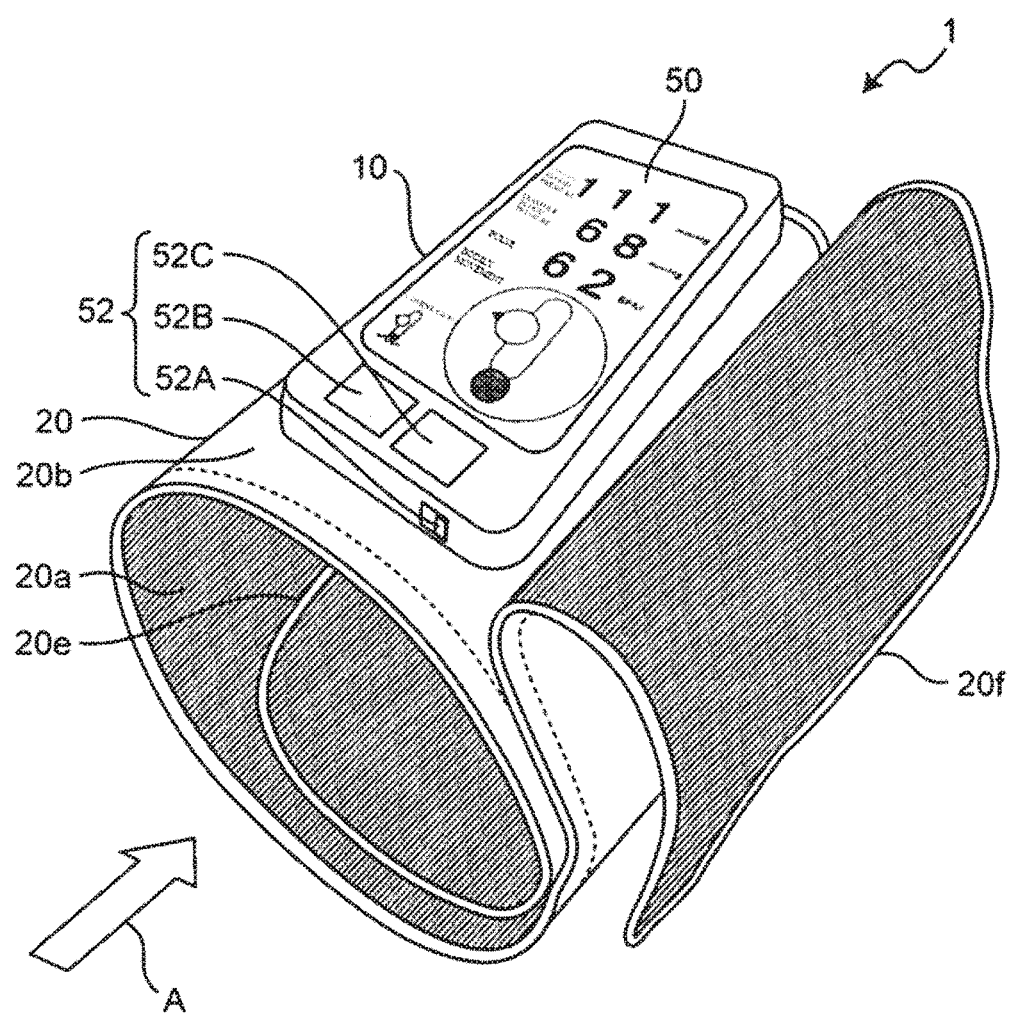
FIG. 1 is a schematic view showing an exterior of a blood pressure monitor in which the cuff and the main body are integrated, and in which a blood pressure related information display apparatus according to an embodiment of the invention is included.

FIG. 1 shows an exterior of an electronic blood pressure monitor (indicated overall by reference numeral 1) according to an embodiment of the invention.

The blood pressure monitor 1 mainly includes a blood pressure measurement cuff 20 that is to be wrapped around a measurement site of a measurement subject, and a main body 10 that is integrally attached to the cuff 20.

The cuff 20 has a shape that is elongated so as to wrap around the measurement site along the circumferential direction, and includes a band-shaped inner cloth 20a that is to come into contact with the measurement site, and an outer cloth 20b that opposes the inner cloth 20a. The inner cloth 20a and the outer cloth 20b are formed into a bladder shape by having their peripheral edges sewn together. The cuff 20 contains a fluid bladder 22 (see FIG. 2) for compressing a measurement site.

In order to form a surface fastener, the surface (inner circumferential surface that is to come into contact with the measurement site) of the inner cloth 20a is provided with many minute hooks (not shown). On the other hand, many minute loops (not shown) that engage with the above-described hooks are formed on the surface (outer circumferential surface) of the outer cloth 20b.

The main body 10 is integrally attached to a site between one end (end portion that is to serve as the inner circumferential end when worn) 20e and another end (end portion that is to serve as the outer circumferential end when worn) 20f with respect to the lengthwise direction (circumferential direction) of the cuff 20.

When the blood pressure monitor 1 is worn on the left upper arm 90a (see FIG. 4A) serving as the measurement site, the left upper arm 90a is arranged in the orientation indicated by the arrow A in FIG. 1 and the cuff 20 is arranged along with the main body 10 on the front surface of the left upper arm 90a. Next, the cuff 20 is wrapped in the form of a left-handed spiral as viewed by the measurement subject. Then, the corresponding surface of the inner cloth 20a is pressed onto and fixed to a site near the inner circumferential end 20e compared to the main body 10 of the outer cloth 20b. The extra portion near the other end 20f in the lengthwise direction (circumferential direction) of the cuff 20 is folded over so as to prevent the main body 10 from being hidden.

Figure 2:
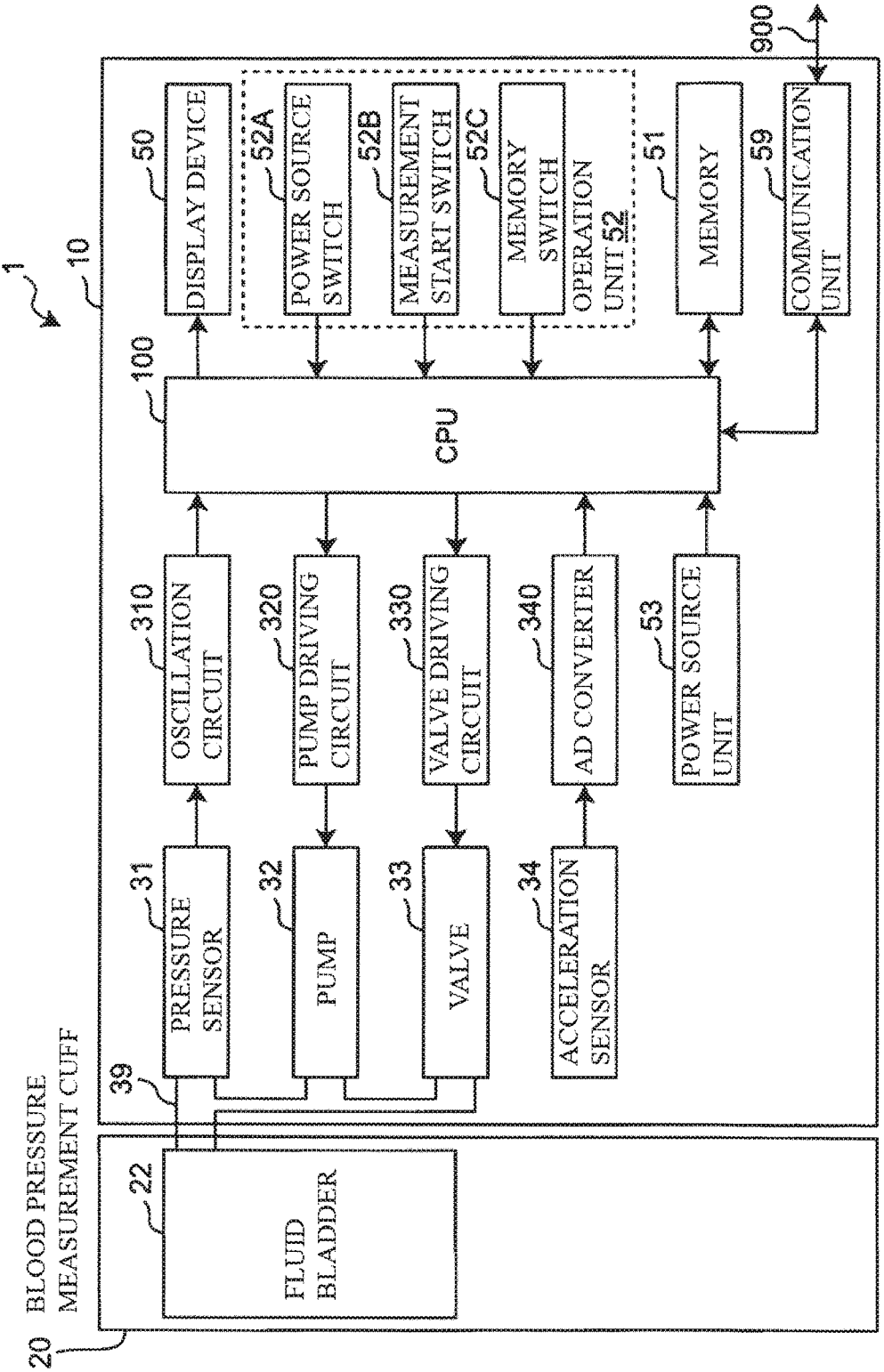
FIG. 2 is a diagram showing a block configuration of the blood pressure monitor.

FIG. 2 shows a schematic block configuration of the cuff 20 and the main body 10 of the blood pressure monitor 1. The blood pressure monitor 1 includes a CPU (Central Processing Unit) 100 serving as a control unit, a display device 50, an operation unit 52, a memory 51 serving as a storage unit, a communication unit 59, a power source unit 53, a pump 32, a valve 33, a pressure sensor 31, and an acceleration sensor 34, all of which are mounted in the main body 10. Furthermore, the main body 10 includes an oscillation circuit 310 that converts the output from the pressure sensor 31 into a frequency, a pump driving circuit 320 that drives the pump 32, a valve driving circuit 330 that drives the valve 33, and an AD converter 340 that performs AD (Analog to Digital) conversion on the output from the acceleration sensor 34, all of which are mounted in the main body 10.

In this example, the display device 50 is composed of an LCD (Liquid Crystal Display) and displays information relating to blood pressure, such as a blood pressure measurement result, in accordance with a control signal from the CPU 100.

The operation unit 52 includes a power source switch 52A for turning on and off the power source of the main body 10, a measurement start switch 52B for receiving an instruction to start blood pressure measurement, and a memory switch 52C for calling a blood pressure measurement result stored in the memory. The switches 52A, 52B, and 52C input operation signals corresponding to instructions performed by a user to the CPU 100.

As shown in FIG. 1, the display device 50 and the operation unit 52 are provided on the front surface (upper surface in FIG. 1) or the side surface of the main body 10.

The memory 51 shown in FIG. 2 stores data of programs for controlling the blood pressure monitor 1, data to be used to control the blood pressure monitor 1, setting data for setting various functions of the blood pressure monitor 1, data of measurement results of blood pressure values, data indicating whether or not there is later-described external compression on the cuff 20, whether or not there is bodily movement of a measurement subject, and the orientation of the measurement subject, and the like. Also, the memory 51 is used as a work memory or the like for when a program is executed.

In accordance with a program for controlling the blood pressure monitor 1 that is stored in the memory 51, the CPU 100 performs control for driving the pump 32 and the valve 33 according to the operation signal from the operation unit 52. Also, based on a signal from the pressure sensor 31, the CPU 100 performs control for calculating the blood pressure values and control for detecting whether or not there is external compression on the cuff 20. Furthermore, based on the output of the acceleration sensor 34, the CPU 100 performs control for detecting whether or not there is bodily movement of the measurement subject and the orientation of the measurement subject. These controls will be described in detail later.

The communication unit 59 is controlled by the CPU 100 to transfer predetermined information to an external apparatus via the network 900, and to receive information from the external apparatus via the network 900 and transfer it to the CPU 100. Communication via the network 900 may be performed wirelessly or using a wire. In this embodiment, the network 900 is the Internet, but there is no limitation to this, and it is also possible to use another type of network such as an in-hospital LAN (Local Area Network), or one-to-one communication using a USB cable or the like.

The power source unit 53 supplies power to the units, namely the CPU 100, the pressure sensor 31, the pump 32, the valve 33, the acceleration sensor 34, the display device 50, the memory 51, the communication unit 59, the oscillation circuit 310, the pump driving circuit 320, the valve driving circuit 330, and the AD converter 340.

The pump 32, the valve 33, and the pressure sensor 31 are connected to the fluid bladder 22 contained in the cuff 20 via a common air tube 39 serving as a tube system. The pump 32 supplies air to the fluid bladder 22 through the air tube 39 in order to increase the pressure (cuff pressure) in the fluid bladder 22 contained in the cuff 20. The valve 33 is a solenoid valve that is controlled so as to open and close through application of a current, and is used to control the cuff pressure by discharging the air in the air bladder 22 through the air tube 39 or sealing the air in the air bladder 22. The pump driving circuit 320 drives the pump 32 based on the control signal provided by the CPU 100. The valve driving circuit 330 opens and closes the valve 33 based on the control signal provided from the CPU 100.

In this example, the pressure sensor 31 is a piezoresistance pressure sensor that detects the pressure of the cuff 20 (fluid bladder 22) through the air tube 39, and in this example, the pressure sensor 31 detects a pressure obtained with reference to atmospheric pressure (with atmospheric pressure being set to zero) and outputs the detected pressure as a cuff pressure signal Pc in a time series. The oscillation circuit 310 oscillates based on an electricity signal value that is based on a change in the electric resistance caused by a piezoresistance effect from the pressure sensor 31, and outputs a frequency signal having a frequency corresponding to the electricity signal value of the pressure sensor 31 to the CPU 100.

In this example, the output of the pressure sensor 31 is used to calculate the blood pressure values (includes systolic blood pressure and diastolic blood pressure; the same applies in the description hereinafter) of the measurement subject 90 through an oscillomertic method. In addition to this, the output of the pressure sensor 31 is used to determine whether or not there is external compression on the cuff 20 by calculating the cuff compliance (amount of air needed to change the cuff pressure by a unit pressure 1 mmHg). Typically, in the case of night-time blood pressure measurement, external compression occurs when the cuff 20 and the left upper arm 90a serving as the measurement site are placed under the torso of the measurement subject who is lying down, and are compressed by the torso and the bed surface.

The acceleration sensor 34 is composed of a triaxial acceleration sensor that is integrally built into the main body 10. The acceleration sensor 34 outputs an acceleration signal indicating acceleration in three mutually orthogonal directions of the main body 10 and accordingly, of the cuff 20 integrally attached to the main body 10, to the CPU 100 via the AD converter 340.

Figure 4A:
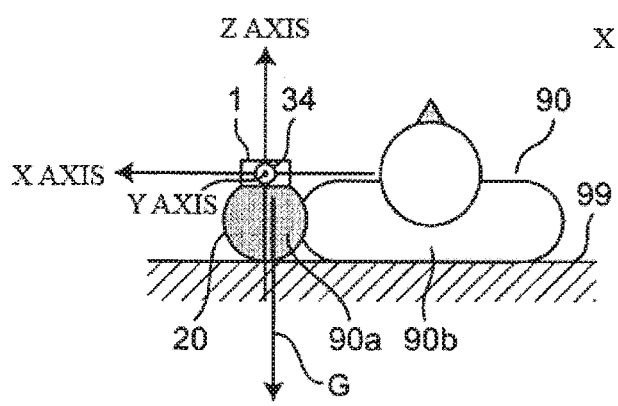
FIG. 4A is a diagram showing a state in which the measurement subject wears the blood pressure monitor on a left upper arm serving as a measurement site and is in a supine orientation (supine position) on a bed surface.
Figure 4B:
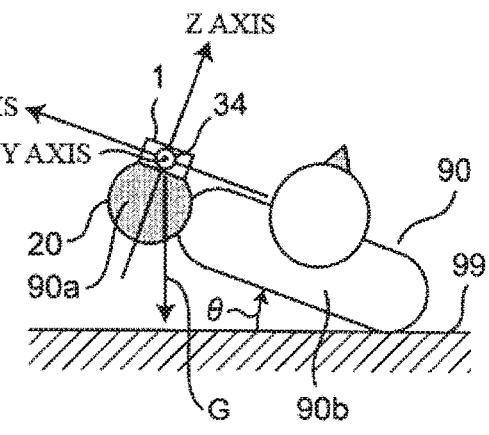
FIG. 4B is a diagram showing a state in which the measurement subject has changed the torso angle with respect to the bed surface from the state of FIG. 4A.

In this example, as shown in FIG. 4A, an XYZ orthogonal coordinate system is set with the position of the acceleration sensor 34 in the main body 10 serving as the origin. The Z axis is set facing outward orthogonally to the front surface of the main body 10. The Y axis is set in an orientation facing from the knee to the shoulder along the left upper arm 90a of the measurement subject 90 in a state in which the blood pressure monitor 1 is worn on the left upper arm 90a serving as the measurement site as described above. Also, the X axis is set orthogonally to the Y axis and the Z axis (the X axis faces approximately leftward as viewed by the measurement subject 90, but this depends on the orientation of the measurement subject 90 as well). Note that in FIG. 4A, the measurement subject 90 is in a supine orientation (supine position) on the bed surface 99, but in actuality, especially in the case of night-time blood pressure measurement, the measurement subject 90 can be in various orientations. For example, as shown in FIG. 4B, the measurement subject can be in an orientation in which the angle θ of the torso is changed with respect to the bed surface 99.

In this example, the output of the acceleration sensor 34 is used to detect whether or not there is bodily movement of the measurement subject 90. In addition, the output of the acceleration sensor 34 is used to detect the orientation of the measurement subject 90 according to the direction (e.g., in FIGS. 4A and 4B, the directions of the gravity acceleration vectors G with respect to the XYZ orthogonal coordinate system are different) of a gravity acceleration vector G with respect to the above-described XYZ orthogonal coordinate system.

Method of Detecting External Compression

Figure 6A:
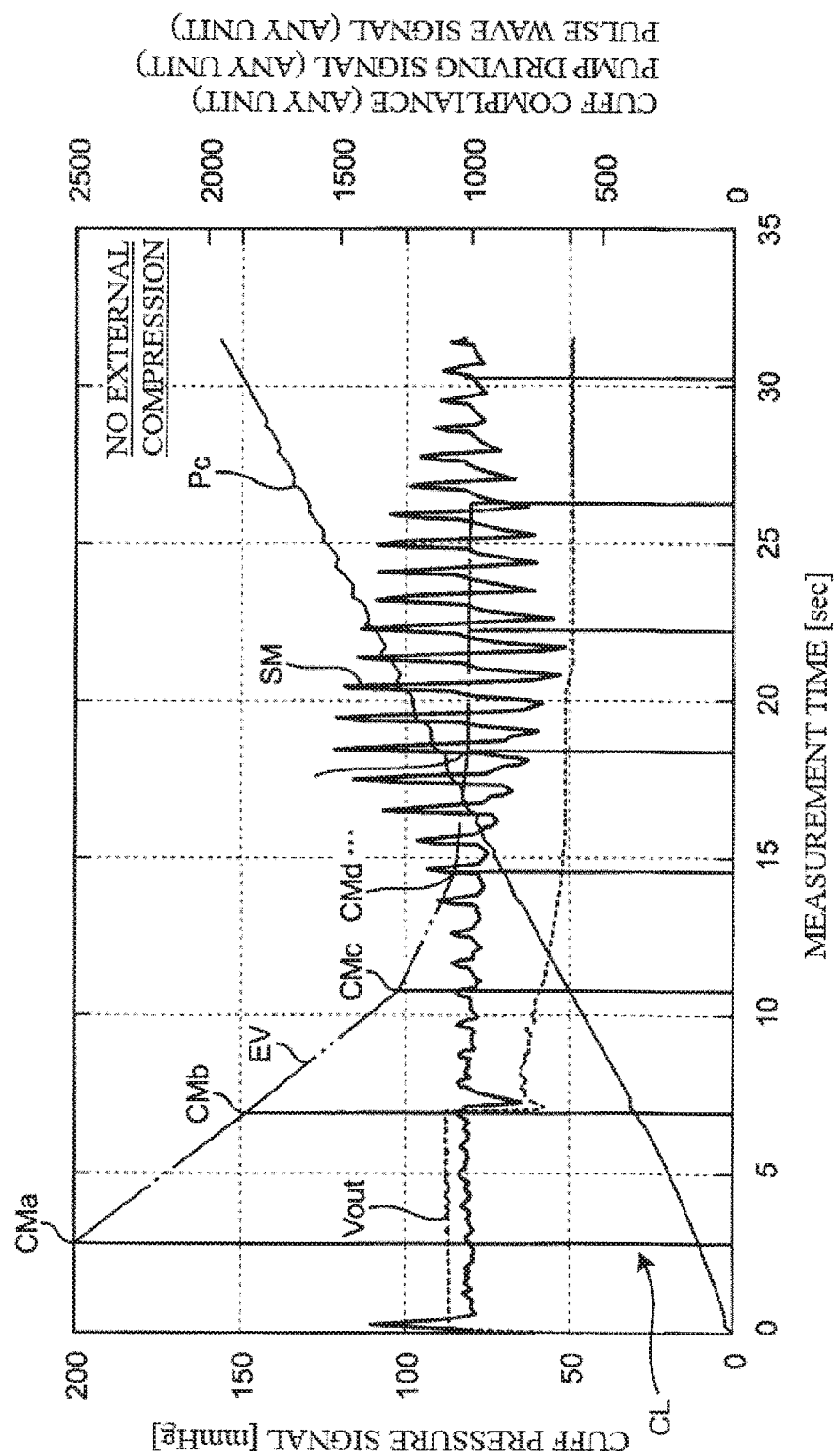
FIG. 6A is a diagram illustrating a cuff pressure signal, a pulse wave signal, a pump driving signal, and a cuff compliance during blood pressure measurement (pressure increase process) in the case where there is no external compression on the cuff of the blood pressure monitor.
Figure 6B:
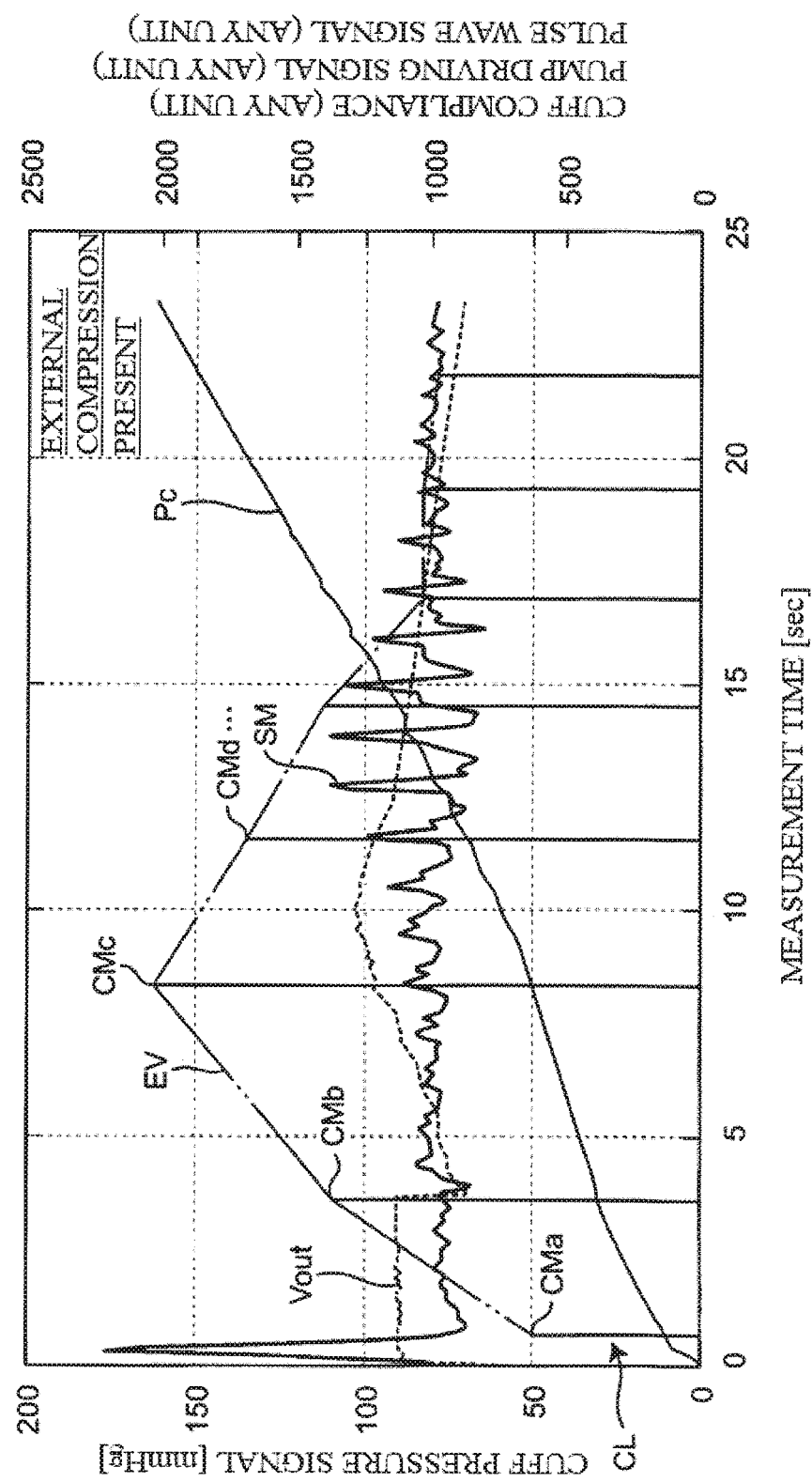
FIG. 6B is a diagram illustrating a cuff pressure signal, a pulse wave signal, a pump driving signal, and a cuff compliance during blood pressure measurement (pressure increase process) in the case where there is external compression on the cuff of the blood pressure monitor (here, a case in which the cuff is placed under the torso of the measurement subject).

FIG. 6A shows a cuff pressure signal Pc, a pulse wave signal SM, a pump driving signal Vout, and a cuff compliance CL during blood pressure measurement (pressure increase process) in the case where there is no external compression on the cuff 20. On the other hand, FIG. 6B shows a cuff pressure signal Pc, a pulse wave signal SM, a pump driving signal Vout, and a cuff compliance CL during blood pressure measurement (pressure increase process) in the case where there is external compression on the cuff 20 (here, a case in which the cuff 20 is placed under the torso of the measurement subject 90). The cuff pressure signal Pc indicates the pressure of the cuff 20 (fluid bladder 22) that is detected via the air tube 39 and the oscillation circuit 310 by the pressure sensor 31. The pulse wave signal SM indicates a signal extracted through a filter (not shown) as a fluctuation component of the cuff pressure signal Pc (the pulse wave signal SM is used to calculate the blood pressure values through an oscillometric method). The pump driving signal Vout indicates a square wave signal (pulse width modulation signal) output from the CPU 100 to the pump driving circuit 320 in order to increase the pressure of the cuff 20. The cuff compliance CL is obtained as values (calculated for each predetermined pressure segment) CMa, CMb, CMc, CMd, . . . , which are obtained by integrating the duty of the pump driving signal Vout over time. In order to facilitate understanding, in FIGS. 6A and 6B, an envelope EV is added to the sequence formed by the values CMa, CMb, CMc, CMd, . . . of the cuff compliance CL.

As can be understood from FIG. 6A, if there is no external compression on the cuff 20, air is supplied to the cuff 20, and the cuff compliance CL gradually decreases and is saturated as pressure increase from the low pressure range (0 mmHg to less than 40 mmHg) to the high pressure range (over 120 mmHg) is performed. The reason for this is because if there is no external compression on the cuff 20, the volume of the cuff easily expands in the low pressure region (0 mmHg to less than 40 mmHg), and therefore a large amount of air is needed to raise the cuff pressure, but the volume of the cuff 20 is substantially less likely to increase when the tensile force of the cuff 20 increases due to the cuff pressure rising by a certain degree. On the other hand, as can be understood from FIG. 6B, if there is external compression on the cuff 20, the cuff compliance CL has a maximum value in the pressure increase process. In this case, in the low pressure region (0 mmHg to less than 40 mmHg), the volume of the cuff 20 increases due to the cuff 20 pressing back on the torso of the measurement subject 90. Accordingly, the cuff compliance CL changes gradually from a low value (varies due to the influence of the tensile force of wrapping the cuff around the measurement site) to a high value. On the other hand, in the high pressure region (over 120 mmHg), the torso is pushed away by the top of the cuff 20 due to the inflation of the cuff 20, and therefore the cuff compliance CL gradually decreases and is saturated, similarly to the case shown in FIG. 6A (the case in which there is no external compression). As a result, in the intermediate range (40 mmHg or more, 120 mmHg or less), the cuff compliance CL has a maximum value accompanying the rising of the cuff pressure.

Accordingly, it is possible to detect whether or not there is external compression on the cuff 20 according to whether or not the cuff compliance CL has a maximum value in the intermediate pressure range (40 mmHg or more and 120 mmHg or less) in the pressure increase process.

Method of Detecting Bodily Movement

Figure 7:
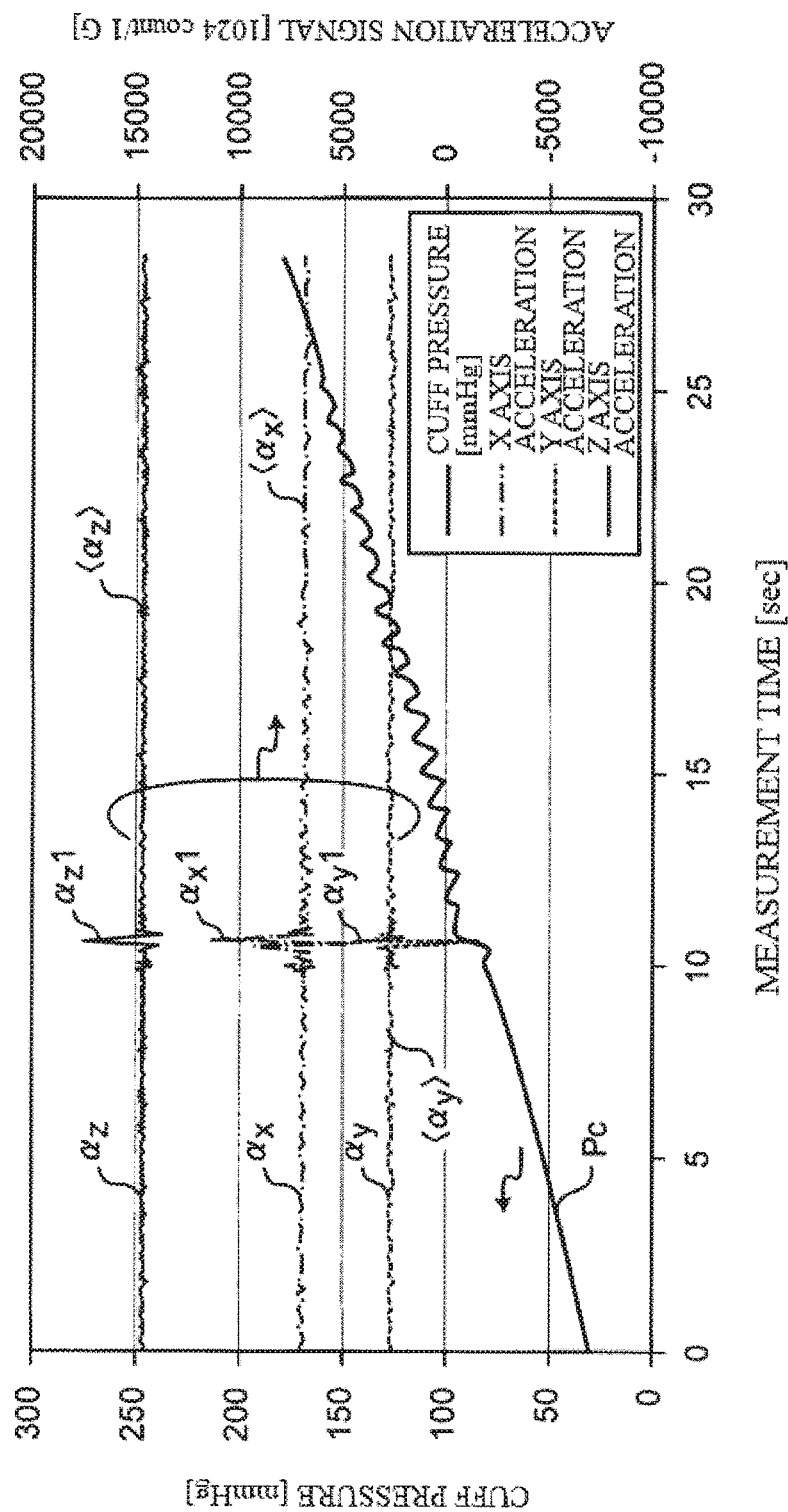
FIG. 7 is a diagram illustrating the output of an acceleration sensor built in the main body, during blood pressure measurement performed by the blood pressure monitor.

FIG. 7 illustrates the outputs (acceleration signals) of the acceleration sensor 34 during blood pressure measurement. During blood pressure measurement, and especially during night-time blood pressure measurement, the measurement subject 90 is essentially in a resting state, and therefore an output $\alpha_x$ in the X-axis direction of the acceleration sensor 34, an output $\alpha_y$ in the Y-axis direction, and an output $\alpha_z$ in the Z-axis direction have approximately constant values. However, if the measurement subject 90 temporarily moves by turning over or the like, the outputs $\alpha_x$, $\alpha_y$, and $\alpha_z$ change as indicated by $\alpha_x 1$, $\alpha_y 1$, and $\alpha_z 1$.

In this example, the CPU 100 functions as a bodily movement detection unit, and during blood pressure measurement, obtains average values $<\alpha_x>$, $<\alpha_y>$, and $<\alpha_z>$ of the outputs $\alpha x$, $\alpha_y$, and $\alpha_z$ of the acceleration sensor 34 in each unit period (e.g., one second or several seconds). Furthermore, the CPU 100 obtains fluctuation amounts $(\alpha_x - <\alpha_x>)$, $(\alpha_y - <\alpha_y>)$, and $(\alpha_z - <\alpha_z>)$ by which the acceleration outputs $\alpha_x$, $\alpha_y$, and $\alpha_z$ of the times in the unit period fluctuate with respect to the average values $<\alpha_x>$, $<\alpha_y>$, and $<\alpha_z>$. Also, when the square root of the sum of squares of these fluctuation amounts $$\{(\alpha_x - <\alpha_x>)^2 + (\alpha_y - <\alpha_y>)^2 + (\alpha_z - <\alpha_z>)^2\}^{1/2}$$

exceeds a predetermined threshold (denoted as Δα), it is determined that there is bodily movement. On the other hand, if the square root of the sum of the squares is less than or equal to the threshold Δα, it is determined that there is no bodily movement.

Accordingly, it is possible to detect whether or not there is bodily movement of the measurement subject 90 based on changes in the outputs of the acceleration sensor 34.

Method of Detecting Orientation

FIGS. 8A to 8H show correspondence relationships between the orientation (torso angle and arm position) of the measurement subject 90 during blood pressure measurement and the normalized outputs (XZ coordinates and XY coordinates) of the acceleration sensor 34.

Figure 8A:
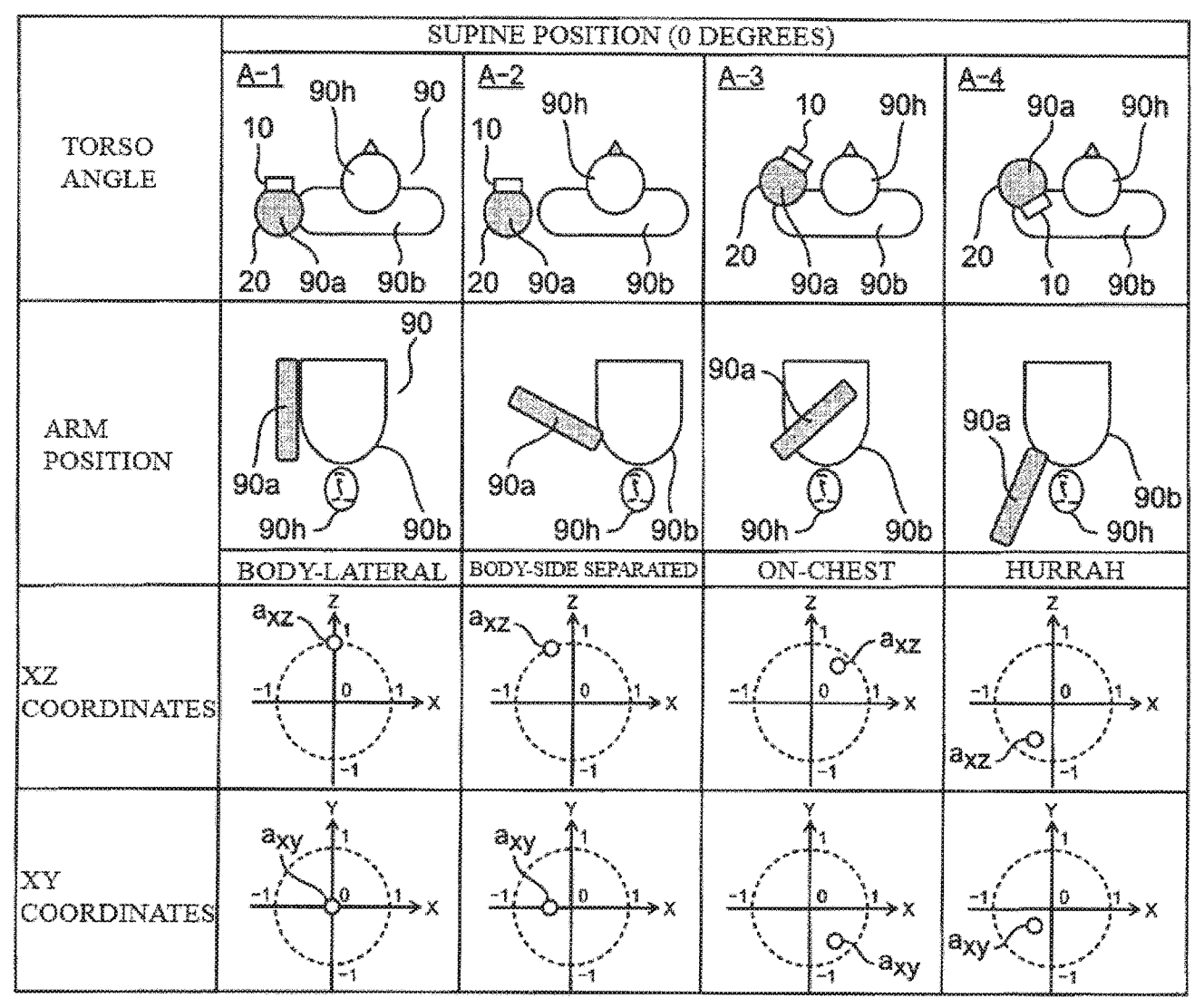
Figure 8B:
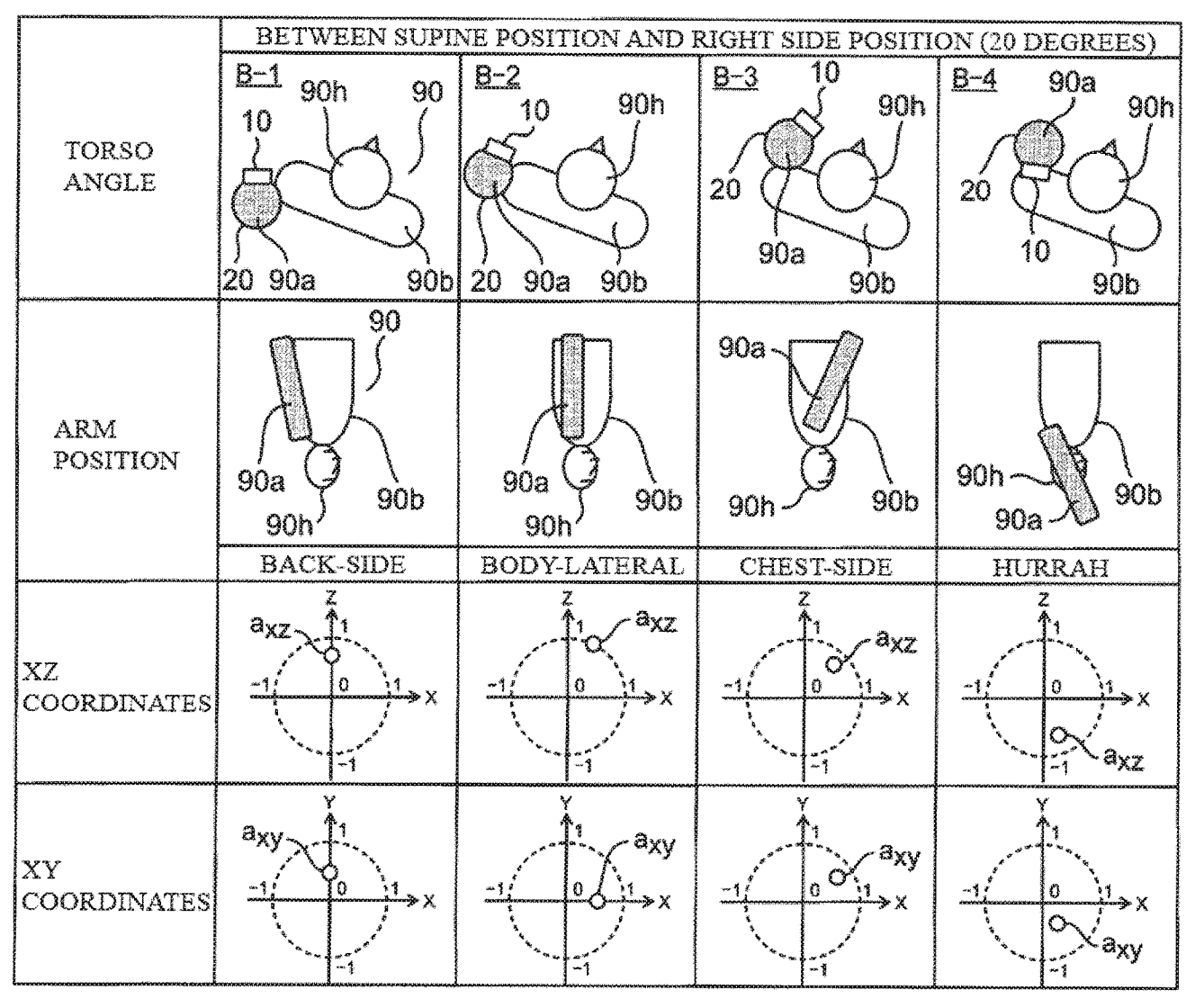
Figure 8C:
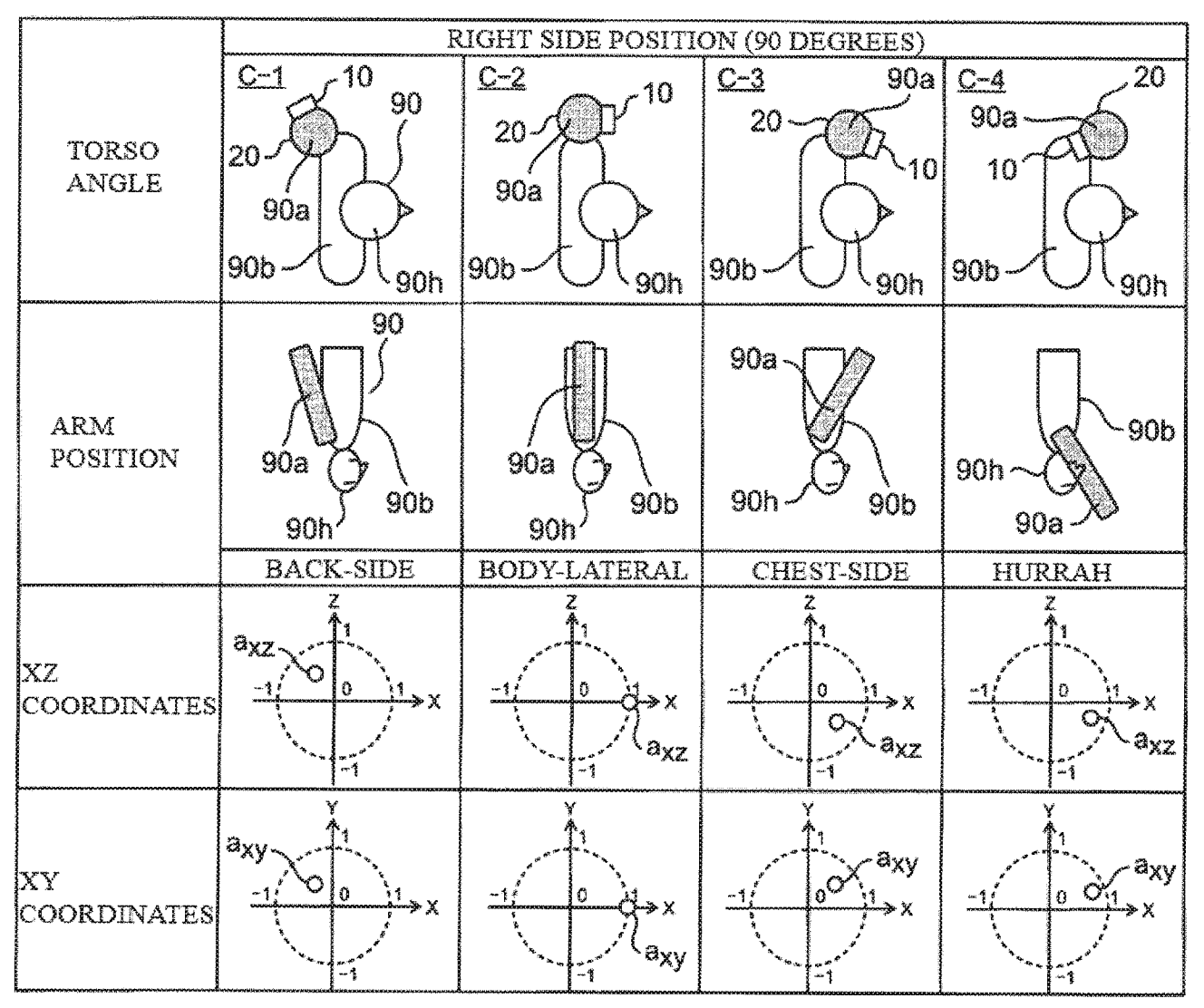
Figure 8D:
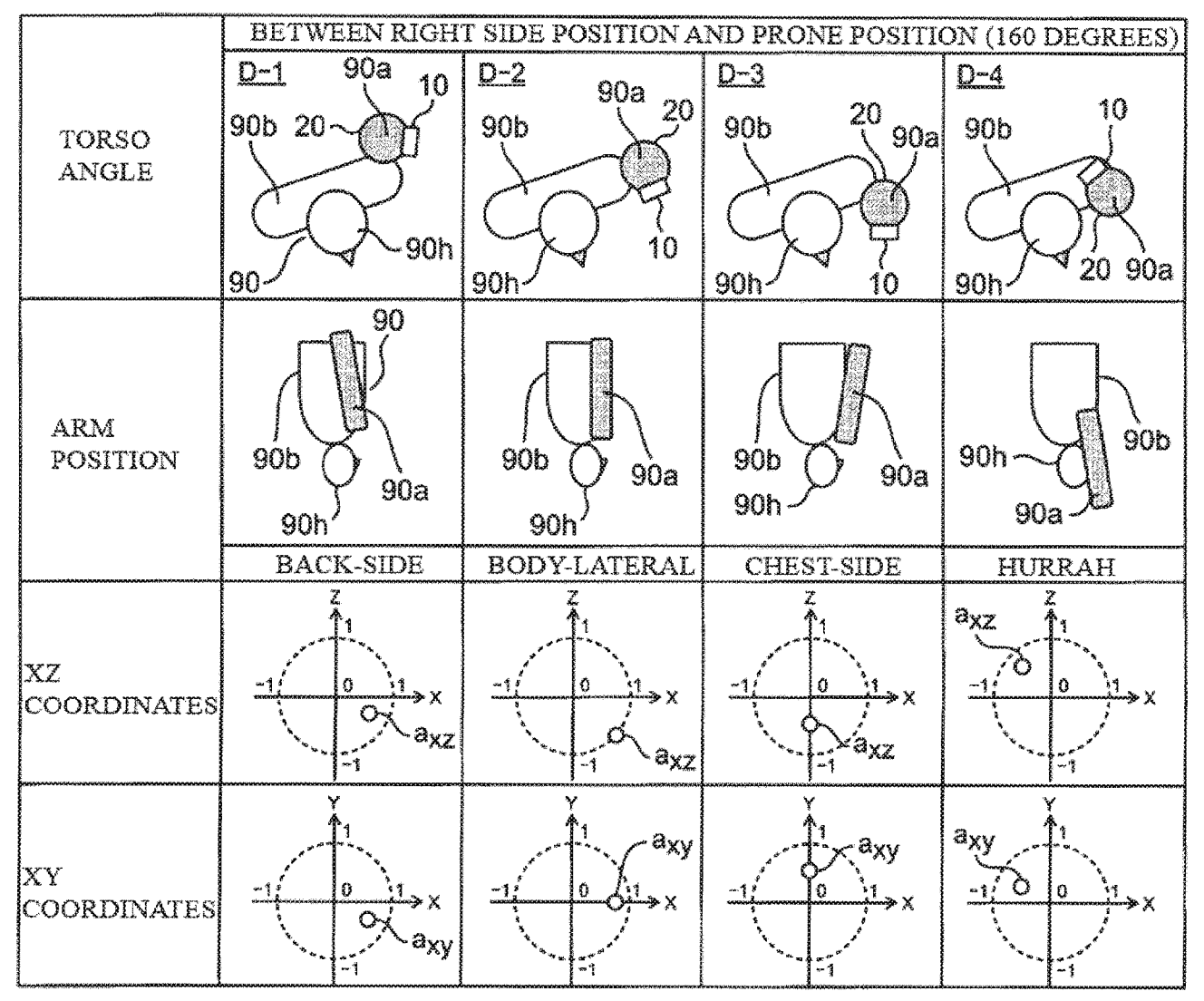
Figure 8E:
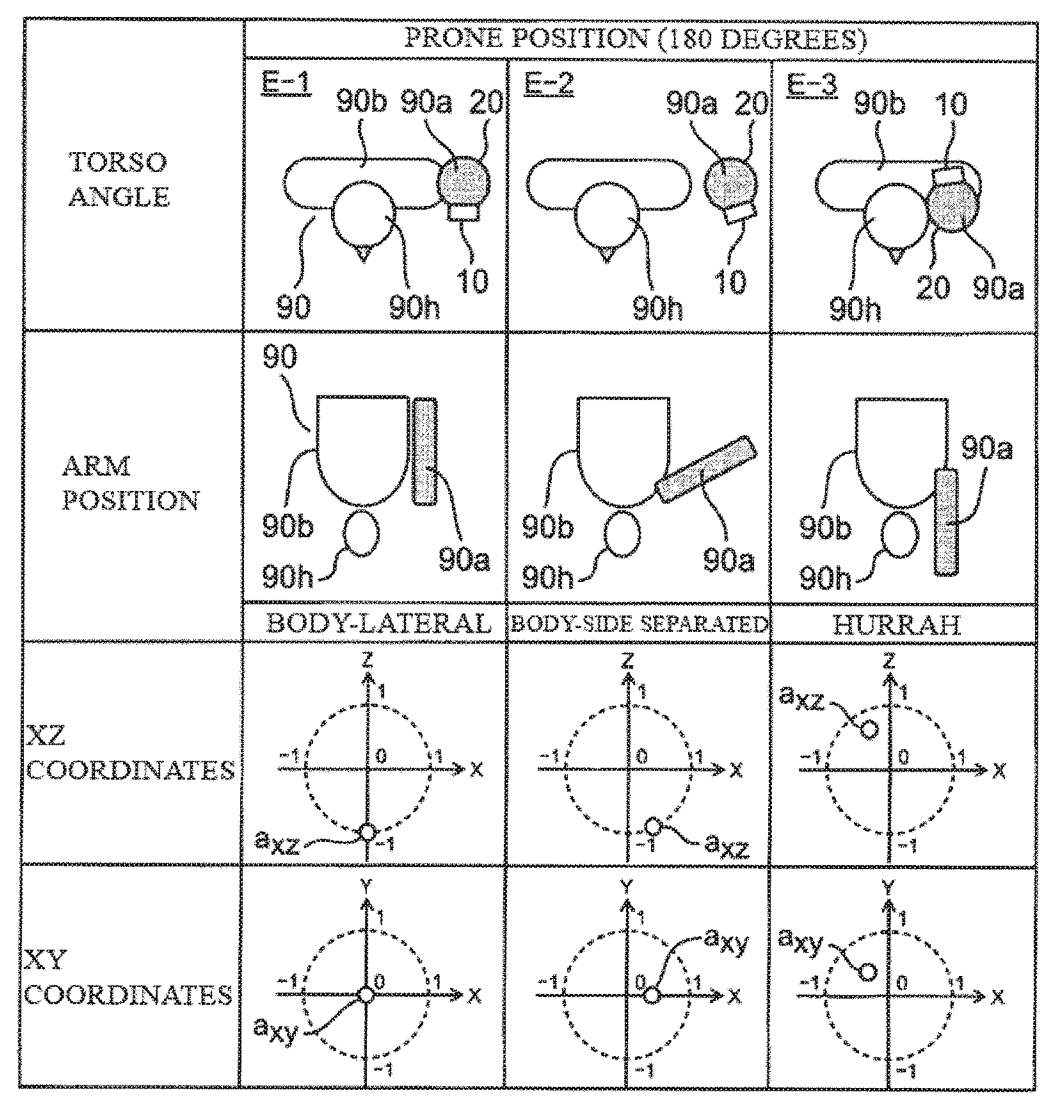
Figure 8F:
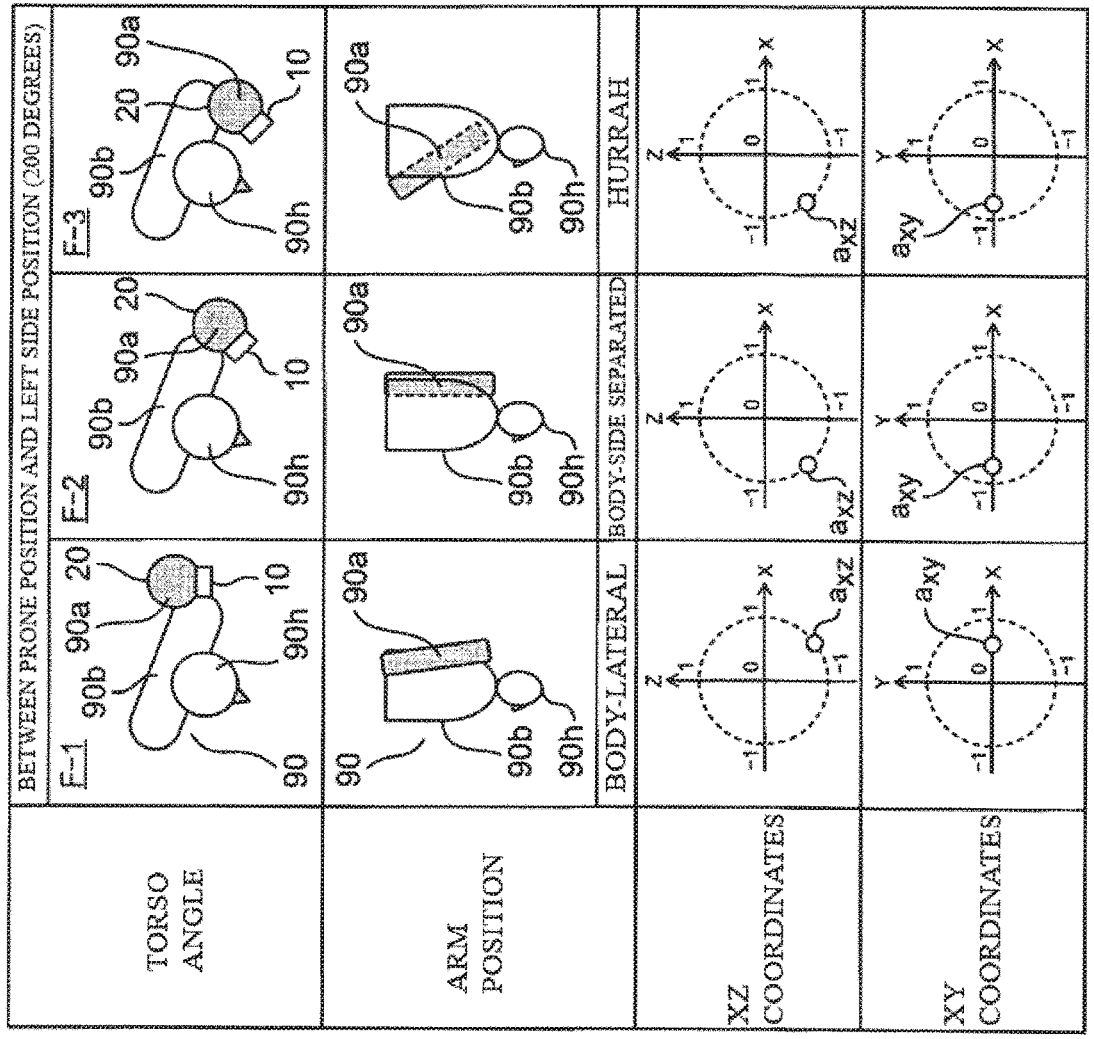
FIG. 8F is a diagram showing a correspondence relationship between the orientation (torso angle and arm position) of the measurement subject during blood pressure measurement and the outputs (XZ coordinates and XY coordinates) of the acceleration sensor.
Figure 8G:
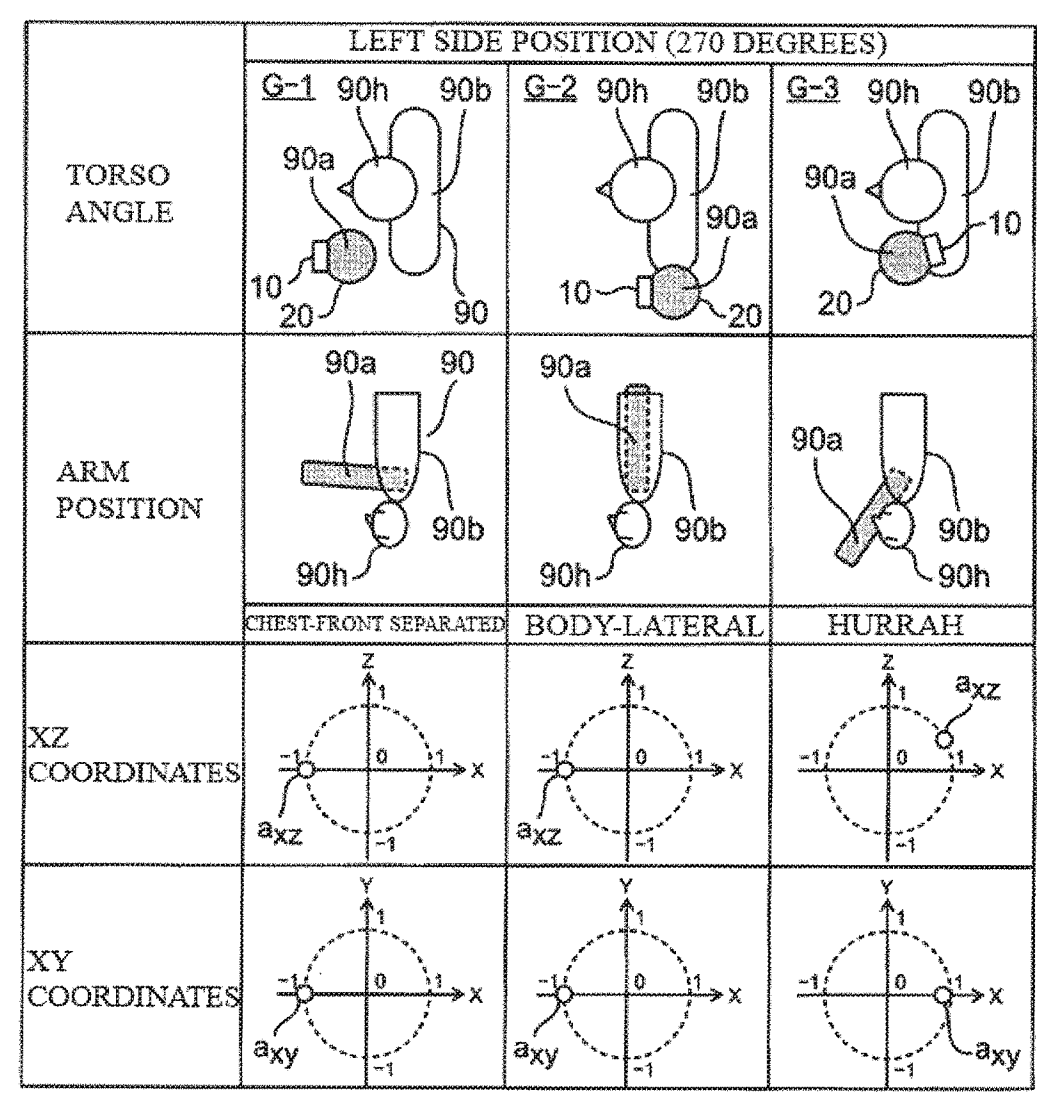
Figure 8H:
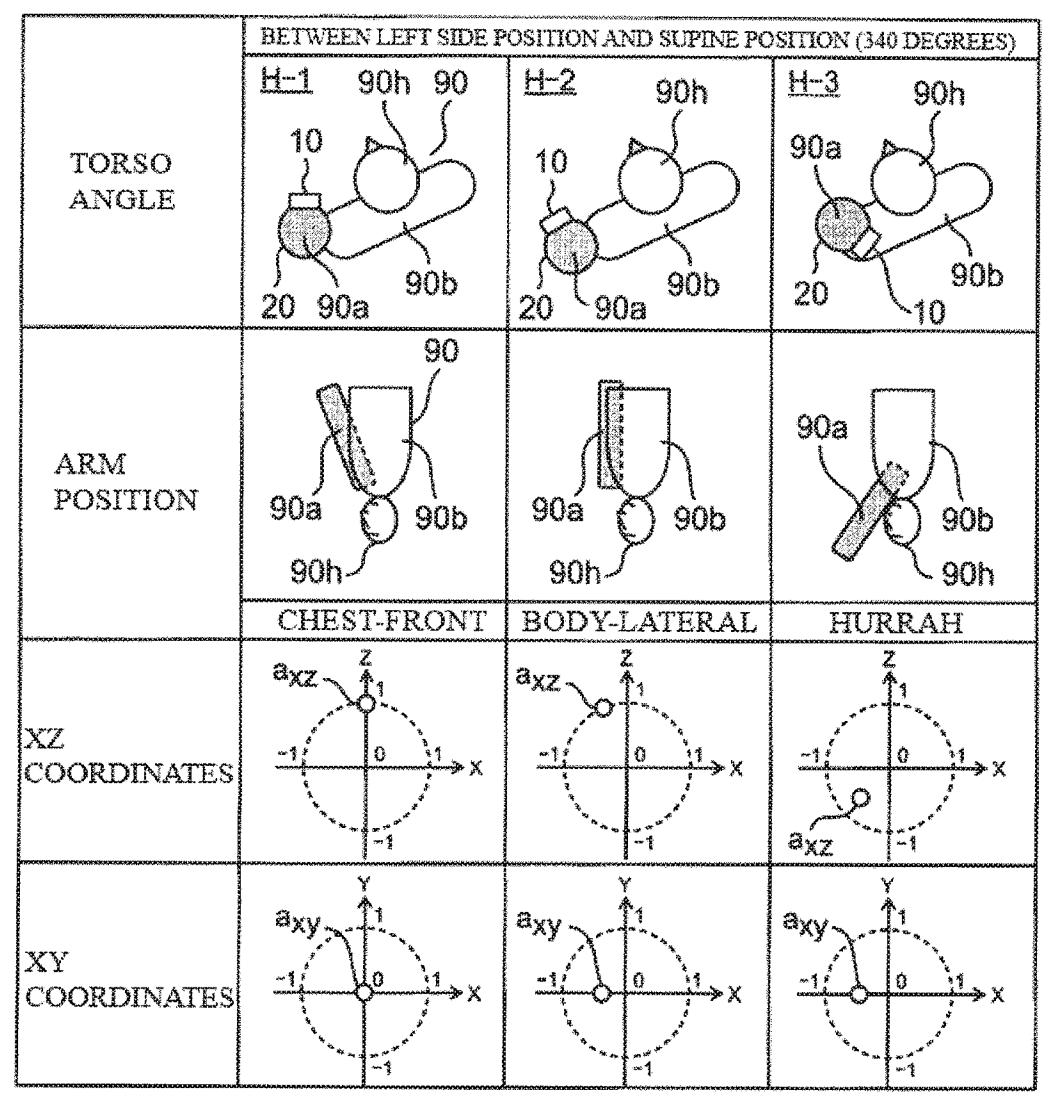

Specifically, FIGS. 8A to 8H show eight types of "torso angles" as torso patterns in the first rows (top rows). "Torso angle" means the angle (indicated by reference numeral θ in FIG. 4B) by which the flat torso 90b is rotated about a center (approximately matches the spine) in a view along the body height direction (in this example, in a view from head to feet) of a person lying on a bed surface. In FIG. 8A, the torso 90b is in the supine position and the torso angle is 0 degrees. In FIG. 8B, the torso 90b is between the supine position and the right side position, and the torso angle is 20 degrees. In FIG. 8C, the torso 90b is in the right side position and the torso angle is 90 degrees. In FIG. 8D, the torso 90b is between the right side position and the prone position, and the torso angle is 160 degrees. In FIG. 8E, the torso 90b is in the prone position and the torso angle is 180 degrees. In FIG. 8F, the torso 90b is between the prone position and the left side position, and the torso angle is 200 degrees. In FIG. 8G, the torso 90b is in the left side position and the torso angle is 270 degrees. In FIG. 8H, the torso 90b is between the left side position and the supine position, and the torso angle is 340 degrees.

Also, in FIGS. 8A to 8H, the second rows each show four or three types of representative arm positions serving as arm patterns corresponding to arm positions that are varied with respect to a person's torso. In FIG. 8A, in the first column (leftmost column), the left upper arm 90a is at a "body-lateral" position of extending along the lateral side of the torso 90b, in the second column, the left upper arm 90a is at a "body-side separated" position of being separated laterally from the torso 90b, in the third column, the left upper arm 90a is at an "on-chest" position of being placed on the torso 90b, and in the fourth column (rightmost column), the left upper arm 90a is in a "hurrah" position of being raised toward the head. In FIGS. 8B, 8C, and 8D, in the first columns (leftmost columns), the left upper arm 90a is at a "back-side" position of being rotated rearward of the torso 90b, in the second columns, the left upper arm 90a is at a "body-lateral" position of extending along the lateral side of the torso 90b, in the third columns, the left upper arm 90a is at a "chest-side" position of being rotated frontward of the torso 90b, and in the fourth columns (rightmost columns), the left upper arm 90a is at a "hurrah" position of being raised toward the head. In FIG. 8E, in the first column (leftmost column), the left upper arm 90a is at a "body-lateral" position of extending along the lateral side of the torso 90b, in the second column, the left upper arm 90a is at a "body-side separated" position of being separated laterally from the torso 90b, and in the third column, (rightmost column), the left upper arm 90a is in a "hurrah" position of being raised toward the head. In FIG. 8F, in the first column (leftmost column), the left upper arm 90a is at a "back-side" position of being rotated rearward of the torso 90b, in the second column, the left upper arm 90a is at a "body-lateral" position of extending along the lateral side of the torso 90b, and in the third column (rightmost column), the left upper arm 90a is at a position of being rotated frontward of the torso 90b. In FIG. 8G, in the first column (leftmost column), the left upper arm 90a is at a "chest-front separated" position of being separated frontward from the torso 90b, in the second column, the left upper arm 90a is at a "body-lateral" position of extending along the lateral side of the torso 90b, and in the third column (rightmost column), the left upper arm 90a is at a "hurrah" position of being raised toward the head. Also, in FIG. 8H, in the first column (leftmost column), the left upper arm 90a is at a "chest-front" position of being rotated frontward from the torso 90b, in the second column, the left upper arm 90a is at a "body-lateral" position of extending along the lateral side of the torso 90b, and in the third column (rightmost column), the left upper arm 90a is at a "hurrah" position of being raised toward the head.

The orientations of the measurement subject 90 during blood pressure measurement (in particular, during nighttime blood pressure measurement) are specified using combinations of the "torso angles" in the first rows (top rows) and the "arm positions" in the second rows corresponding thereto in FIGS. 8A to 8H.

In the third rows and the fourth rows (bottom rows) in FIGS. 8A to 8H, the normalized (normalized to 1) outputs of the acceleration sensor 34 in cases where the measurement subject 90 is in orientations specified using combinations of the "torso angles" in the first rows and the "arm positions" in the second rows are indicated in XZ coordinate planes and XY coordinate planes. Here, the measurement subject 90 is substantially in a resting state, and the outputs (the above-described average values $<\alpha_x>$, $<\alpha_y>$, and $<\alpha_z>$) of the acceleration sensor 34 correspond to the direction of the gravity acceleration vector G corresponding to the XYZ orthogonal coordinate system set in the main body 10.

For example, if the measurement subject 90 is in an orientation specified using a combination in which the "torso angle" is 0 degrees and the "arm position" is "body-lateral" in the first column (leftmost column) of FIG. 8A, the normalized outputs of the acceleration sensor 34 are detected as point $a_{xz}$ where X=0 and Z=1 in the XZ coordinate plane in the third row, and as point $a_{xy}$ where X=0 and Y=0 in the XY coordinate plane in the fourth row. Also, when the measurement subject 90 is in an orientation specified using the combination in which the "torso angle" is 0 degrees and the "arm position" is "body-side separated" in the second column of FIG. 8A, the normalized outputs of the acceleration sensor 34 are detected as point $a_{xz}$ where −1<X<0 and 0<Z<1 (second quadrant) in the XZ coordinate plane in the third row, and as point $a_{xy}$ where −1<X<0 and Y=0 in the XY coordinate plane in the fourth row. When the measurement subject 90 is in an orientation specified using the combination in which the "torso angle" is 0 degrees and the "arm position" is "on-chest" in the third column of FIG. 8A, the normalized outputs of the acceleration sensor 34 are detected as point $a_{xz}$ where 0<X<1 and 0<Z<1 (first quadrant) in the XZ coordinate plane in the third row, and as point $a_{xy}$ where 0<X<1 and −1<Y<0 (fourth quadrant) are satisfied in the XY coordinate plane in the fourth row. When the measurement subject 90 is in an orientation specified using the combination in which the "torso angle" is 0 degrees and the "arm position" is "hurrah" in the fourth column (rightmost column) of FIG. 8A, the normalized outputs of the acceleration sensor 34 are detected as point $a_{xz}$ where −1<X<0 and −1<Z<0 (third quadrant) in the XZ coordinate plane in the third row, and as point $a_{xy}$ where −1<X<0 and −1<Y<0 (third quadrant) in the XY coordinate plane in the fourth row.

Also, for example, if the measurement subject 90 is in an orientation specified using the combination in which the "torso angle" is 270 degrees and the "arm position" is "chest-front separated" in the first column (leftmost column) in FIG. 8G, the normalized outputs of the acceleration sensor 34 are detected as point $a_{xz}$ where X=−1 and Z=0 in the XZ coordinate plane in the third row, and as point $a_{xy}$ where X=−1 and Y=0 in the XY coordinate plane in the fourth row. Also, if the measurement subject 90 is in an orientation specified using the combination in which the "torso angle" is 270 degrees and the "arm position" is "body-lateral" in the second column in FIG. 8G, the normalized outputs of the acceleration sensor 34 are detected as point $a_{xz}$ where X=−1 and Z=0 in the XZ coordinate plane in the third row, and as point $a_{xy}$ where X=−1 and Y=0 in the XY coordinate plane in the fourth row. If the measurement subject 90 is in an orientation specified using the combination in which the "torso angle" is 270 degrees and the "arm position" is "hurrah" in the third column (rightmost column) in FIG. 8G, the normalized output of the acceleration sensor 34 is detected as point $a_{xz}$ where 0<X<1 and 0<Z<1 (first quadrant) in the XZ coordinate plane in the third row, and as point $a_{xy}$ where 0<X<1 and Y=0 in the XY coordinate plane in the fourth row.

As can be understood from the examples above, in FIGS. 8A to 8H, when the measurement subject 90 is in an orientation specified using a combination of a "torso angle" in a first row and an "arm position" in a second row, the orientation and the normalized output (combination of XZ coordinates and XY coordinates) of the acceleration sensor 34 are in a one-to-one correspondence. Accordingly, if the normalized outputs (combination of the XZ coordinates and the XY coordinates) of the acceleration sensor 34 are specified, the orientation of the measurement subject 90, that is, the combination of the "torso angle" and the "arm position" is specified. In other words, the orientation of the measurement subject 90 is determined. In this example, the CPU 100 functions as an orientation detection unit and determines the orientation of the measurement subject 90 based on the outputs (the above-described average values $<a_x>$, $<a_y>$, and $<a_z>$ are desirable) of the acceleration sensor 34. Accordingly, the orientation of the measurement subject can be detected easily.

With the blood pressure monitor 1, in order to express the orientation of the measurement subject 90 specified based on the output of the acceleration sensor 34, illustrations A-1 to A-4 shown in the first row in FIG. 8A, illustrations B-1 to B-4 shown in the first row in FIG. 8B, illustrations C-1 to C-4 shown in the first row in FIG. 8C, illustrations D-1 to D-4 shown in the first row in FIG. 8D, illustrations E-1 to E-3 shown in the first row in FIG. 8E, illustrations F-1 to F-3 shown in the first row in FIG. 8F, illustrations G-1 to G-3 shown in the first row in FIG. 8G, and illustrations H-1 to H-3 shown in the first row in FIG. 8H are prepared in advance. These illustrations A-1 to A-4, B-1 to B-4, C-1 to C-4, D-1 to D-4, E-1 to E-3, F-1 to F-3, G-1 to G-3, and H-1 to H-3 correspond to combinations obtained using the torso patterns and arm patterns as materials.

In these illustrations A-1 to A-4, B-1 to B-4, C-1 to C-4, D-1 to D-4, E-1 to E-3, F-1 to F-3, G-1 to G-3, and H-1 to H-3, the torso 90b of the measurement subject 90 is expressed as an elongated circle. In the approximate center in the long axis direction of the elongated circle indicating the torso 90b, the head 90h of the measurement subject 90 is indicated by a circle and a small triangle corresponding to the nose, in a state of being overlaid slightly shifted in the short axis direction. Also, the left upper arm 90a around which the cuff 20 is wrapped is indicated by a circle on the left side of the elongated circle indicating the torso 90b. The main body 10 attached integrally to the cuff 20 is indicated by a rectangle.

For example, in the illustration A-1 shown in FIG. 8A, the elongated circle indicating the torso 90b is extended in the horizontal direction so as to indicate that the torso angle is 0 degrees (supine position). The circle indicating the head 90h of the measurement subject 90 is overlaid shifted upward of the elongated circle indicating the torso 90b (note that up, down, left, and right in this paragraph indicate up, down, left, and right in FIG. 8A). The circle indicating the left upper arm 90a is adjacent to the left of the elongated circle indicating the torso 90b so as to indicate "body-lateral". The rectangle indicating the main body 10 is located on the upper portion of the circle indicating the left upper arm 90a so as to indicate that the main body 10 is on the front surface of the left upper arm 90a. In the illustration A-2, the circle indicating the left upper arm 90a is separated from the elongated circle indicating the torso 90b so as to indicate "body-side separated". In the illustration A-3, the circle indicating the left upper arm 90a is located above and to the left of the elongated circle indicating the torso 90b so as to indicate "on-chest". In the illustration A-4, the circle indicating the left upper arm 90a is located above and to the left of the elongated circle indicating the torso 90b and the rectangle indicating the main body 10 is located below the circle indicating the left upper arm 90a so as to indicate "hurrah". The other portions of the illustrations A-2 to A-4 are drawn in the same manner as those of the illustration A-1.

Also, for example, in the illustration G-1 shown in FIG. 8G, the elongated circle indicating the torso 90b is elongated in the vertical direction so as to indicate that the torso angle is 270 degrees (left side position). The circle indicating the head 90h of the measurement subject 90 is overlaid shifted to the left of the elongated circle indicating the torso 90b (note that up, down, left, and right in this paragraph indicate up, down, left, and right in FIG. 8G). The circle indicating the left upper arm 90a is separated from the elongated circle indicating the torso 90b so as to indicate "chest-front separated". The rectangle indicating the main body 10 is located on the left portion of the circle indicating the left upper arm 90a so as to indicate that the main body 10 is on the front surface of the left upper arm 90a. In the illustration G-2, the circle indicating the left upper arm 90a is adjacent to the bottom of the elongated circle indicating the torso 90b so as to indicate "body-lateral". In the illustration G-3, the circle indicating the left upper arm 90a is located downward and to the left of the elongated circle indicating the torso 90b and the rectangle indicating the main body 10 is located on the right portion of the circle indicating the left upper arm 90a so as to indicate "hurrah". The other portions of the illustrations G-2 to G-3 are drawn in the same manner as those of the illustration G-1.

In this manner, the orientation of the measurement subject 90 can be schematically indicated using the illustrations A-1 to A-4, B-1 to B-4, C-1 to C-4, D-1 to D-4, E-1 to E-3, F-1 to F-3, G-1 to G-3, and H-1 to H-3, that is, as a combination of a torso pattern indicating the "torso angle" and an arm pattern indicating the "arm position".

With the blood pressure monitor 1, the normalized outputs (XZ coordinates and XY coordinates) of the acceleration sensor 34 in the third rows and the fourth rows in FIGS. 8A to 8H and the illustrations A-1 to A-4, B-1 to B-4, C-1 to C-4, D-1 to D-4, E-1 to E-3, F-1 to F-3, G-1 to G-3, and H-1 to H-3 in the first rows are stored in a one-to-one correspondence as an orientation table in the memory 51. Thus, by preparing various illustrations indicating orientations of the measurement subject 90 in advance, image data including an illustration of an orientation of the measurement subject 90 can be created rapidly with simple processing during later-described display processing (step ST110 in FIG. 5).

Overall Operation

Figure 5:
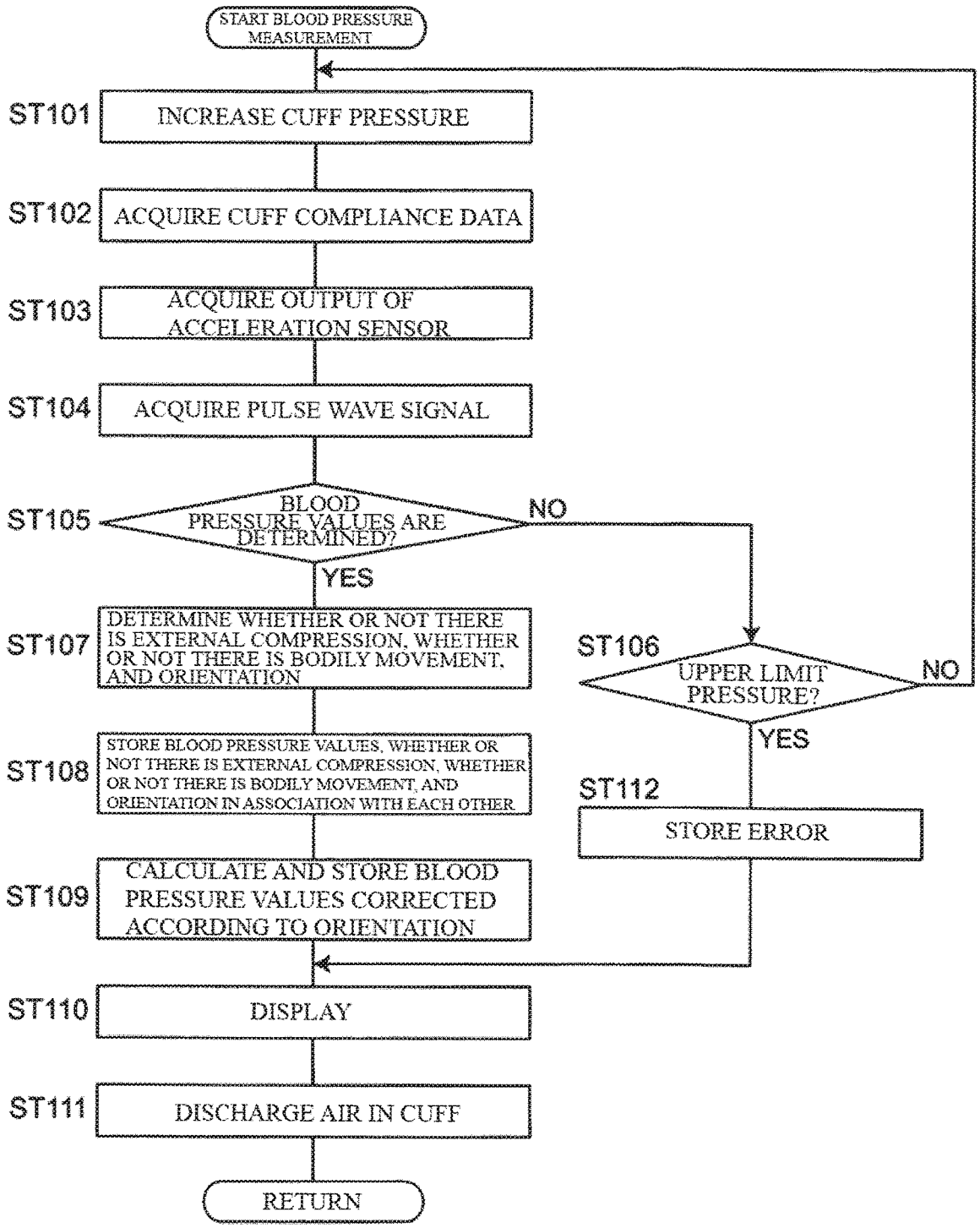
FIG. 5 is a diagram showing an overall operation flow of the blood pressure monitor.

FIG. 5 illustrates an overall operation flow of the blood pressure monitor 1.

If the measurement start switch 52B is pressed in a state in which the power source switch 52A is on, or if a predetermined measurement timing is reached in the case of night-time blood pressure measurement, the blood pressure monitor 1 starts the blood pressure measurement. At the start of blood pressure measurement, the CPU 100 initializes a memory region for processing and outputs a control signal to the valve driving circuit 330. Based on the control signal, the valve driving circuit 330 opens the valve 33 to discharge the air in the fluid bladder 22 of the cuff 20. Next, control for adjusting the pressure sensor 31 to 0 mmHg is performed.

When the blood pressure measurement is started, first, the CPU 100 closes the valve 33 via the valve driving circuit 330, and thereafter drives the pump 32 via the pump driving circuit 320 while monitoring the cuff pressure signal Pc using the pressure sensor 31 (and the air tube 39 and the oscillation circuit 310), and thus performs control for sending air to the fluid bladder 22. Accordingly, the fluid bladder 22 is inflated and the cuff pressure gradually increases (step ST101).

In the pressure increase process, in order to detect whether or not there is external compression on the cuff 20, the CPU 100 integrates the pump driving signal Vout for the pump driving circuit 320 to acquire data indicating the cuff compliance CL, as illustrated in FIGS. 6A and 6B (step ST102).

Also, in the pressure increase process, in order to detect whether or not there is bodily movement of the measurement subject 90 and the orientation of the measurement subject 90, the CPU 100 acquires the outputs of the acceleration sensor 34 (step ST 103).

Also, in this example, in the pressure increase process, in order to calculate the blood pressure values, the CPU 100 acquires the pulse wave signal SM serving as a fluctuation component through a filter (not shown) from the cuff pressure signal Pc (step ST104).

Next, the CPU 100 functions as a blood pressure measurement unit and attempts calculation of the blood pressure values (systolic blood pressure SBP and diastolic blood pressure DBP) and the pulse by applying a known algorithm through the oscillometric method based on the pulse wave signal SM acquired at this time point (step ST105).

At this time point, if the blood pressure values cannot yet be calculated due to insufficient data (NO in step ST105), the processing of steps ST101 to ST105 are repeated as long as the cuff pressure has not reached the upper limit pressure (in the interest of safety, the upper limit pressure is set in advance to 300 mmHg, for example) (NO in step ST106).

When the blood pressure values and pulse can be thus calculated (YES in step ST105), the processing advances to step ST107, and the CPU 100 detects whether or not there is external compression on the cuff 20, whether or not there is bodily movement of the measurement subject 90, and the orientation of the measurement subject 90.

Here, the CPU 100 functions as an external compression detection unit and detects whether or not there is external compression on the cuff 20 based on whether or not the cuff compliance CL is at a maximum value in the pressure increase process. Specifically, when the cuff compliance CL decreases monotonically as illustrated in FIG. 6A in the pressure increase process, it is determined that there is no external compression. On the other hand, when the cuff compliance CL has a maximum value as illustrated in FIG. 6B in the pressure increase process, it is determined that there is external compression.

Also, the CPU 100 functions as a bodily movement detection unit and detects whether or not there is bodily movement of the measurement subject 90 based on changes in the output of the acceleration sensor 34. Specifically, in each unit period (e.g., one second or multiple seconds) in the pressure increase process, the CPU 100 obtains the average values $<\alpha_x>$, $<\alpha_y>$, and $<\alpha_z>$ of the outputs $\alpha_x$, $\alpha_y$, and $\alpha_z$ of the acceleration sensor 34 illustrated in FIG. 7. Then, when the square root of the sum of squares of the fluctuation amounts of the acceleration outputs $\alpha_x$, $\alpha_y$, and $\alpha_z$ in the unit period $$\{(\alpha_x - <\alpha_x>)^2 + (\alpha_y - <\alpha_y>)^2 + (\alpha_z - <\alpha_z>)^2\}^{1/2}$$

exceeds a predetermined threshold $\Delta\alpha$, it is determined that there is bodily movement. On the other hand, if the square root of the sum of the squares is less than or equal to the threshold $\Delta\alpha$, it is determined that there is no bodily movement.

Also, the CPU 100 functions as an orientation detection unit and detects the orientation of the measurement subject 90 based on the outputs (the above-described average values $<\alpha_x>$, $<\alpha_y>$, $<\alpha_z>$) of the acceleration sensor 34 in the pressure increase process. Specifically, the CPU 100 determines whether or not the orientation of the measurement subject 90 corresponds to an orientation in an illustration in one of the first rows (top rows) in FIGS. 8A to 8H based on the correspondence relationship between the normalized outputs (XZ coordinates and XY coordinates) of the acceleration sensor 34 in the third rows and fourth rows of FIGS. 8A to 8H and the illustrations A-1 to A-4, B-1 to B-4, C-1 to C-4, D-1 to D-4, E-1 to E-3, F-1 to F-3, G-1 to G-3, and H-1 to H-3 in the first rows, which are stored in the orientation table in the memory 51.

Next, in step ST108 in FIG. 5, the CPU 100 stores the measurement number, measurement time, measured blood pressure values (systolic blood pressure SBP and diastolic blood pressure DBP), pulse, whether or not there is external compression on the cuff 20, whether or not there is bodily movement of the measurement subject 90, and the orientation of the measurement subject 90, in association with each other in the memory 51.

Here, the data stored in the memory 51 is accumulated for each measurement of the blood pressure, as shown in the following data table (Table 1) for example. In this example, the night-time blood pressure measurement is performed every 30 seconds.

TABLE 1

Data table

| | | | | | | | | Correction according to altitude difference | | |
|---|---|---|---|---|---|---|---|---|---|---|
| Measurement number | Measurement time | Systolic blood pressure SBP [mmHg] | Diastolic blood pressure DBP [mmHg] | Pulse [BPM] | External compression | Bodily movement | Orientation | Correction amount [mmHg] | Systolic blood pressure SBP' [mmHg] | Diastolic blood pressure DBP' [mmHg] |
| 0 | 23:00 | 125 | 93 | 64 | 0 | 0 | K-1 | 0 | 125 | 93 |
| 1 | 23:30 | 117 | 81 | 55 | 0 | 0 | A-1 | 0 | 117 | 81 |
| 2 | 0:00 | 111 | 77 | 55 | 0 | 0 | A-1 | 0 | 111 | 77 |
| 3 | 0:30 | 107 | 71 | 62 | 0 | 0 | C-2 | 16 | 123 | 87 |
| 4 | 1:00 | 99 | 71 | 55 | 0 | 1 | C-2 | 16 | 115 | 87 |
| 5 | 1:30 | 103 | 65 | 57 | 0 | 0 | B-2 | 8 | 111 | 73 |
| 6 | 2:00 | 105 | 69 | 54 | 0 | 0 | B-2 | 8 | 113 | 77 |
| 7 | 2:30 | 111 | 68 | 62 | 1 | 0 | G-2 | 0 | 111 | 68 |
| 8 | 3:00 | 131 | 85 | 55 | 0 | 1 | A-1 | 0 | 131 | 85 |

TABLE 1-continued

Data table

| Measurement number | Measurement time | Systolic blood pressure SBP [mmHg] | Diastolic blood pressure DBP [mmHg] | Pulse [BPM] | External compression | Bodily movement | Orientation | Correction according to altitude difference | | |
|---|---|---|---|---|---|---|---|---|---|---|
| | | | | | | | | Correction amount [mmHg] | Systolic blood pressure SBP' [mmHg] | Diastolic blood pressure DBP' [mmHg] |
| 9 | 3:30 | 105 | 71 | 47 | 0 | 0 | A-3 | 10 | 115 | 81 |
| 10 | 4:00 | 119 | 81 | 55 | 0 | 0 | A-1 | 0 | 119 | 81 |
| 11 | 4:30 | 119 | 81 | 50 | 0 | 0 | B-2 | 8 | 127 | 89 |
| 12 | 5:00 | 118 | 82 | 54 | 0 | 0 | C-2 | 16 | 134 | 98 |
| 13 | 5:30 | 114 | 79 | 55 | 0 | 0 | C-2 | 16 | 130 | 95 |
| 14 | 6:00 | 121 | 83 | 53 | 0 | 0 | B-2 | 8 | 129 | 91 |
| ... | ... | ... | ... | ... | ... | ... | ... | ... | ... | ... |

Here, in the "external compression" column, "1" indicates that there is external compression and "0" indicates that there is no external compression. In the "bodily movement" column, "1" indicates that there is bodily movement and "0" indicates that there is no bodily movement. In the "orientation" column, the orientation of the measurement subject 90 is indicated by the reference sign specifying an illustration in a first row (top row) of FIGS. 8A to 8H. Note that the reference sign "K-1" in the "orientation" column indicates an orientation (e.g., an orientation corresponding to the first illustration K-1 in later-described FIG. 15) in which the measurement subject 90 is in a sitting position and the left upper arm 90a serving as the measurement site naturally hangs downward. Although not shown in the third and fourth rows of FIGS. 8A to 8H, the orientation K-1 is detected as the point at which X=0 and Z=0 in the XZ coordinate plane and is detected as the point at which X=0 and Y=1 in the XY coordinate plane. The "correction using altitude difference" column will be described later.

Next, in step ST109 in FIG. 5, the CPU 100 functions as a blood pressure correction unit and corrects the measured blood pressure values according to the obtained orientation of the measurement subject 90.

As is known, the measured blood pressure values are shifted from the actual values (values in the case where the heart and the measurement site are at the same height level) according to an altitude difference between the heart and the measurement site (in this example, the left upper arm 90a) of the measurement subject 90. In view of this, a correction amount that is thought to be suitable due to experience is set in advance according to the obtained orientation of the measurement subject 90, as shown in the "correction amount" column in "correction according to altitude difference" of the data table (Table 1). For example, with the orientation "A-1", the heart and the left upper arm 90a of the measurement subject 90 are at the same height level, and therefore the correction amount is set to 0 [mmHg]. With the orientation "C-2", the left upper arm 90a is at a higher level than the heart of the measurement subject 90, and therefore the correction amount is set to 16 [mmHg]. Also, with the orientation "B-2", the altitude difference between the heart and the left upper arm 90a of the measurement subject 90 is at a level between that of the orientation "A-1" and that of the orientation "C-2", and therefore the correction amount is set to 8 [mmHg].

Then, the CPU 100 adds the pre-set correction amount to the measured blood pressure value according to the obtained orientation of the measurement subject 90. For example, if the obtained orientation is "C-2", 16 [mmHg] is added as the correction amount when the measurement blood pressure values are systolic blood pressure SBP=107 [mmHg] and diastolic blood pressure DBP=71 [mmHg], for example. As a result, the corrected blood pressure values are systolic blood pressure SBP'=123 [mmHg] and diastolic blood pressure DBP'=87 [mmHg]. Also, if the obtained orientation is "B-2", 8 [mmHg] is added as the correction amount when the measurement blood pressure values are systolic blood pressure SBP=103 [mmHg] and diastolic blood pressure DBP=65 [mmHg], for example. As a result, the corrected blood pressure values are systolic blood pressure SBP'=111 [mmHg] and diastolic blood pressure DBP'=73 [mmHg]. Note that if the obtained orientation is "A-1", the correction amount is 0 [mmHg], and therefore values that are the same as those of the systolic blood pressure SBP and the diastolic blood pressure DBP go in the "systolic blood pressure SBP" and "diastolic blood pressure DBP" columns of the data table (Table 1).

In this example, the CPU 100 additionally stores the correction amount corresponding to the orientation and the corrected blood pressure values (systolic blood pressure SBP' and diastolic blood pressure DBP') in the data table (Table 1) in the memory 51 in association with the measurement number, the measurement time, the measured blood pressure values (systolic blood pressure SBP and diastolic blood pressure DBP), the pulse, whether or not there is external compression on the cuff 20, whether or not there is bodily movement of the measurement subject 90, and the orientation of the measurement subject 90.

Next, in step ST110 in FIG. 5, the CPU 100 refers to the data table (Table 1) in the memory 51, functions as a notification unit, and displays the blood pressure values (systolic blood pressure SBP and diastolic blood pressure DBP) measured in this instance of measurement, the pulse, whether or not there is external compression on the cuff 20, whether or not there is bodily movement of the measurement subject 90, and the orientation of the measurement subject 90 on the display screen of the display device 50.

Finally, in step ST111 in FIG. 5, the CPU 100 performs control for opening the valve 33 via the valve driving circuit 330 and discharging the air in the fluid bladder 22 of the cuff 20.

Note that in the flow shown in FIG. 5, the acquisition of the cuff compliance data, the acquisition of the output of the acceleration sensor, the acquisition of the pulse wave signal, and the calculation of the blood pressure values are performed in the process of increasing the pressure of the cuff 20, but there is no limitation to this. The acquisition of the output of the acceleration sensor, the acquisition of the pulse wave signal, and the calculation of the blood pressure values may be performed in the pressure decrease process.

Example of Display in Blood Pressure Monitor Main Body

As shown in FIGS. 9A, 9B, 10A, and 10B, a "systolic blood pressure" region 50a for displaying the measured systolic blood pressure SBP as a numerical value, a "diastolic blood pressure" region 50b for displaying the measured diastolic blood pressure DBP as a numerical value, a "pulse" region 50c for displaying the pulse as a numerical value, a "bodily movement" region 50d for displaying whether or not there is bodily movement of the measurement subject as an illustration as bodily movement information, a "compression" region 50e for displaying whether or not there is external compression on the cuff 20 as an illustration as compression information, and an orientation region 50f for displaying the orientation of the measurement subject 90 as an illustration are set on the display screen of the display device 50. An illustration J-1 indicating that there is bodily movement is composed of a circle m1 indicating the head of the measurement subject 90, a rounded-corner rectangle (a rectangle with rounded corners) m2 indicating the torso of the measurement subject 90, and a waveform mark m3 indicating motion of the body. Also, the illustration J-2 indicating that there is external compression is obtained approximately by adding a waveform mark m4 indicating the bed surface to the illustration G-2. The illustrations J-1 and J-2 are stored in advance in the memory 51. Note that when there is no bodily movement, the "bodily movement" region 50d is blank (empty) and when there is no external compression, the "compression" region 50e is blank (empty). The illustration corresponding to the content (reference numeral specifying the illustration) of the "orientation" column of the data table (Table 1) is selected from among the multiple illustrations A-1 to A-4, B-1 to B-4, C-1 to C-4, D-1 to D-4, E-1 to E-3, F-1 to F-3, G-1 to G-3, and H-1 to H-3 in the first rows (top rows) in FIGS. 8A to 8H, and is displayed in the orientation region 50f. Accordingly, the image data including the illustration indicating the orientation of the measurement subject 90 can be rapidly created with simple processing.

In the example shown in FIG. 9A, a systolic blood pressure SBP of 115 mmHg, a diastolic blood pressure DBP of 87 mmHg, and a pulse of 70 BPM that were measured in this instance of measuring are displayed as numerical values in the "systolic blood pressure" region 50a, the "diastolic blood pressure" region 50b, and the "pulse" region 50c. Also, the fact that there is bodily movement is displayed as an illustration J-1 in the "bodily movement" region 50d. The fact that there is external compression is displayed as an illustration J-2 in the "compression" region 50e. Furthermore, the orientation of the measurement subject 90 is displayed as the illustration G-2 in the orientation region 50f.

In the example shown in FIG. 9B, a systolic blood pressure SBP of 117 mmHg, a diastolic blood pressure DBP of 81 mmHg, and a pulse of 70 BPM that were measured in the current instance of measurement are displayed as numerical values in the "systolic blood pressure" region 50a, the "diastolic blood pressure" region 50b, and the "pulse" region 50c, similarly to the example above. Also, the fact that there is no bodily movement is displayed as a blank in the "bodily movement" region 50d. The fact that there is no external compression is displayed as a blank in the "compression" region 50e. Furthermore, the orientation of the measurement subject 90 is displayed as an illustration A-1 in the orientation region 50f.

Figure 10A:
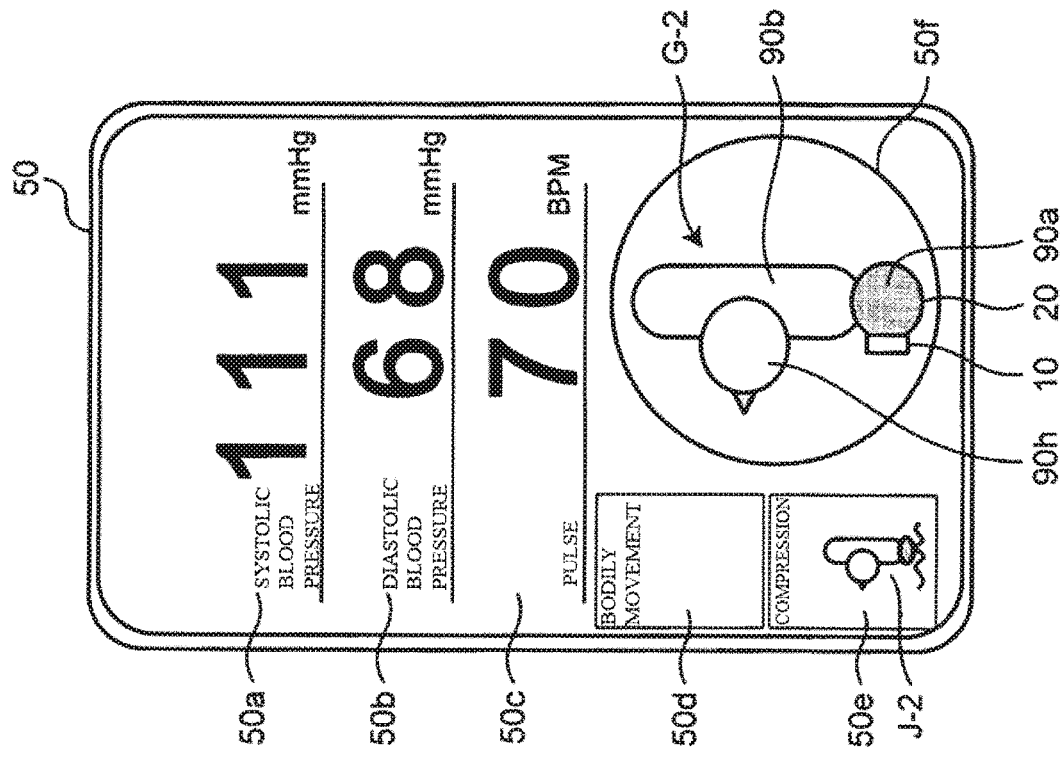
FIGS. 10A and 10B are diagrams illustrating images to be displayed on the display device of the blood pressure monitor.

In the example shown in FIG. 10A, similarly to the example above, a systolic blood pressure SBP of 111 mmHg, a diastolic blood pressure DBP of 68 mmHg, and a pulse of 70 BPM that were measured in the current instance of measurement are displayed as numerical values in the "systolic blood pressure" region 50a, the "diastolic blood pressure" region 50b, and the "pulse" region 50c. Also, the fact that there is no bodily movement is displayed as a blank in the "bodily movement" region 50d. The fact that there is external compression is displayed as the illustration J-2 in the "compression" region 50e. Furthermore, the orientation of the measurement subject 90 is displayed as the illustration G-2 in the orientation region 50f.

Figure 10B:
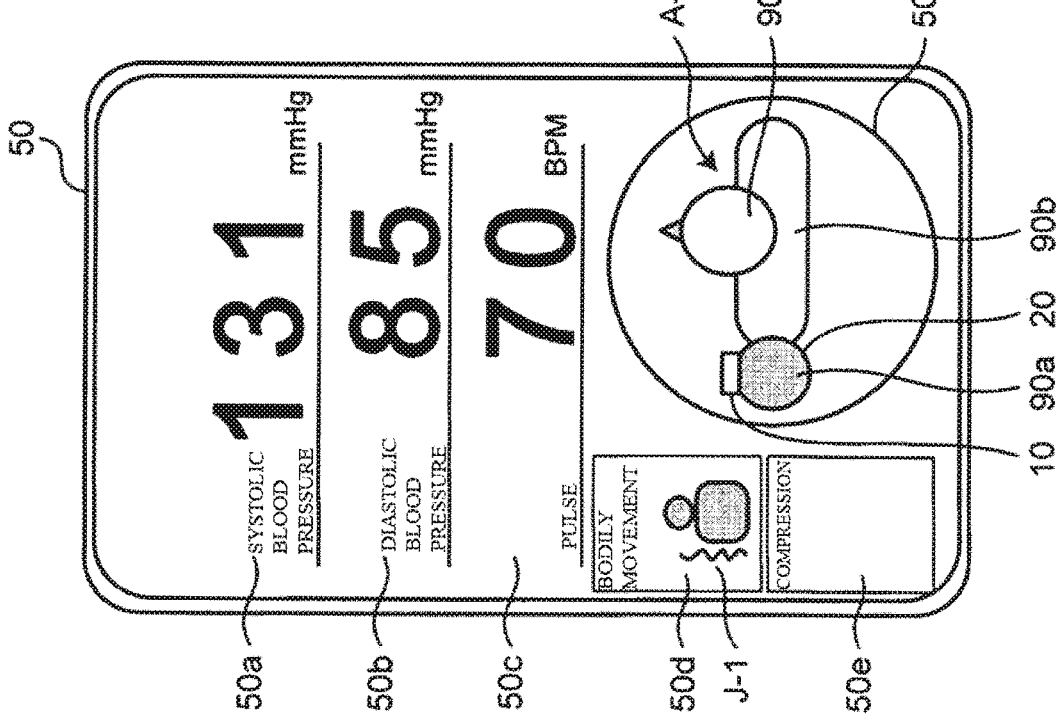

In the example shown in FIG. 10B, similarly to the example above, a systolic blood pressure SBP of 131 mmHg, a diastolic blood pressure DBP of 85 mmHg, and a pulse of 70 BPM that were measured in the current instance of measurement are displayed as numerical values in the "systolic blood pressure" region 50a, the "diastolic blood pressure" region 50b, and the "pulse" region 50c. Also, the fact that there is bodily movement is displayed as the illustration J-1 in the "bodily movement" region 50d. The fact that there is no external compression is displayed as a blank in the "compression" region 50e. Furthermore, the orientation of the measurement subject 90 is displayed as the illustration A-1 in the orientation region 50f.

Accordingly, the user can find out the blood pressure values (systolic blood pressure SBP and diastolic blood pressure DBP) and the value of the pulse that were measured in this instant of measurement by viewing the numerical values in the "systolic blood pressure" region 50a, the "diastolic blood pressure" region 50b, and the "pulse" region 50c on the display screen of the display device 50. In addition to this, by viewing the illustrations in the "bodily movement" region 50d, the "compression" region 50e, and the orientation region 50f, the user can intuitively understand whether or not there is bodily movement of the measurement subject 90, whether or not there is external compression on the cuff 20, and the orientation of the measurement subject 90 during blood pressure measurement.

Note that in the pressure increase process shown in FIG. 5, if the cuff pressure reaches the upper limit value while the blood pressure values cannot be calculated (YES in step ST106), the fact that an error occurred is stored in the memory 51 in association with the measurement time (step ST112). In this example, "Error" is stored in the columns for the measured blood pressure values (systolic blood pressure SBP and diastolic blood pressure DBP) in the data table (Table 1) in the memory 51. Even if this error is present, it is desirable to store the detection results in the "external compression" column, the "bodily movement" column, and the "orientation" column of the data table (Table 1), if possible. The reason for this is that there is a possibility that the cause of the error is due to the external compression, bodily movement, or orientation. Also, in step ST110 in FIG. 5, "Error" is displayed as character strings in the "systolic blood pressure" region 50a and the "diastolic blood pressure" region 50b on the display screen of the display device 50 in this example, and illustrations indicating the detection results are displayed in the "bodily movement" region 50d, the "compression" region 50e, and the orientation region 50f. In this type of case, the user can infer the cause of the error by viewing the illustrations in the "bodily movement" region 50d, the "compression" region 50e, and the orientation region 50f.

Specific Method of Detecting External Compression

Figure 14A:
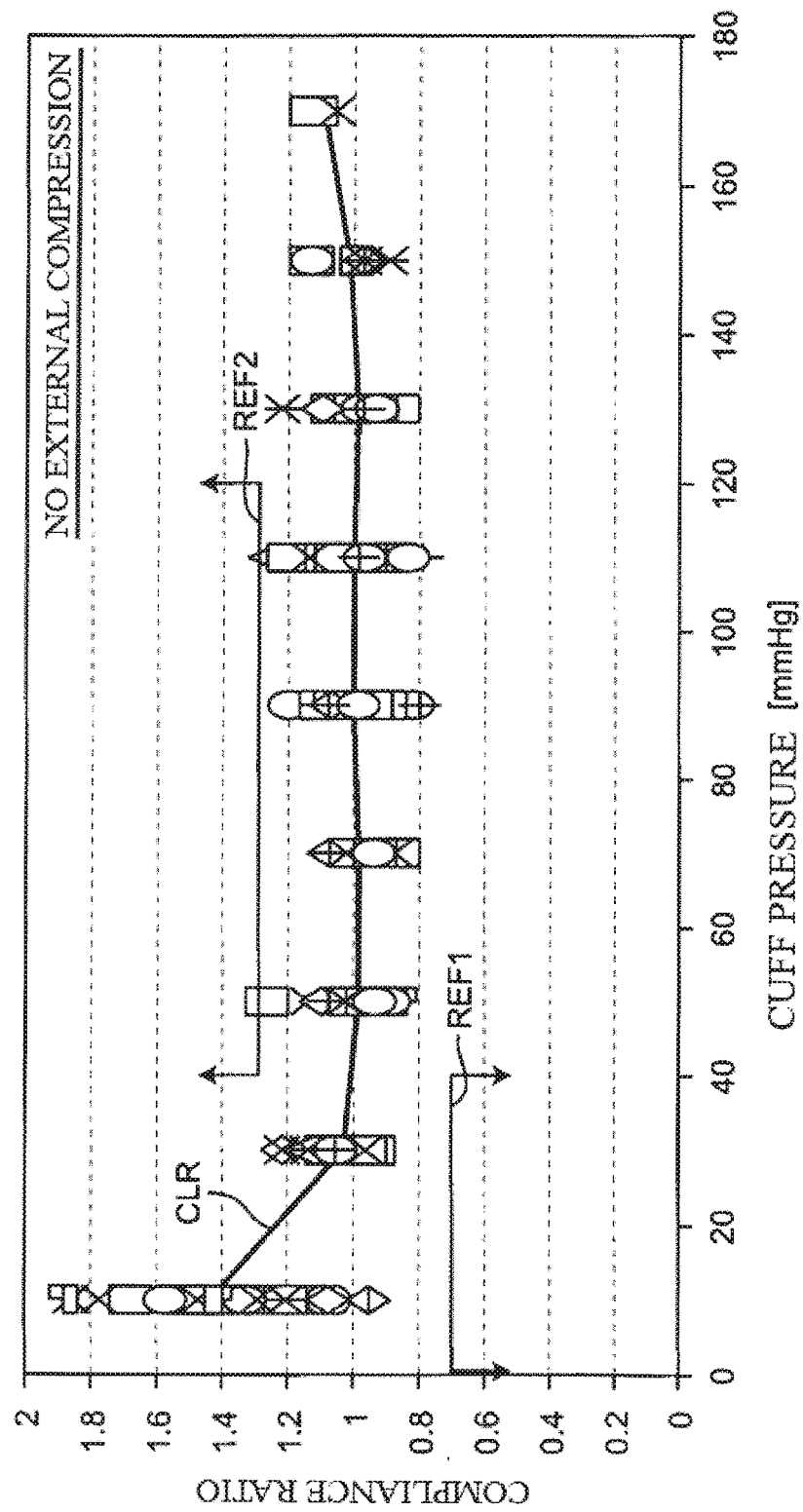
FIG. 14A is a diagram showing a change in the compliance ratio accompanying a change in the cuff pressure during blood pressure measurement (pressure increase process) in the case where there is no external compression on the cuff.
Figure 14B:
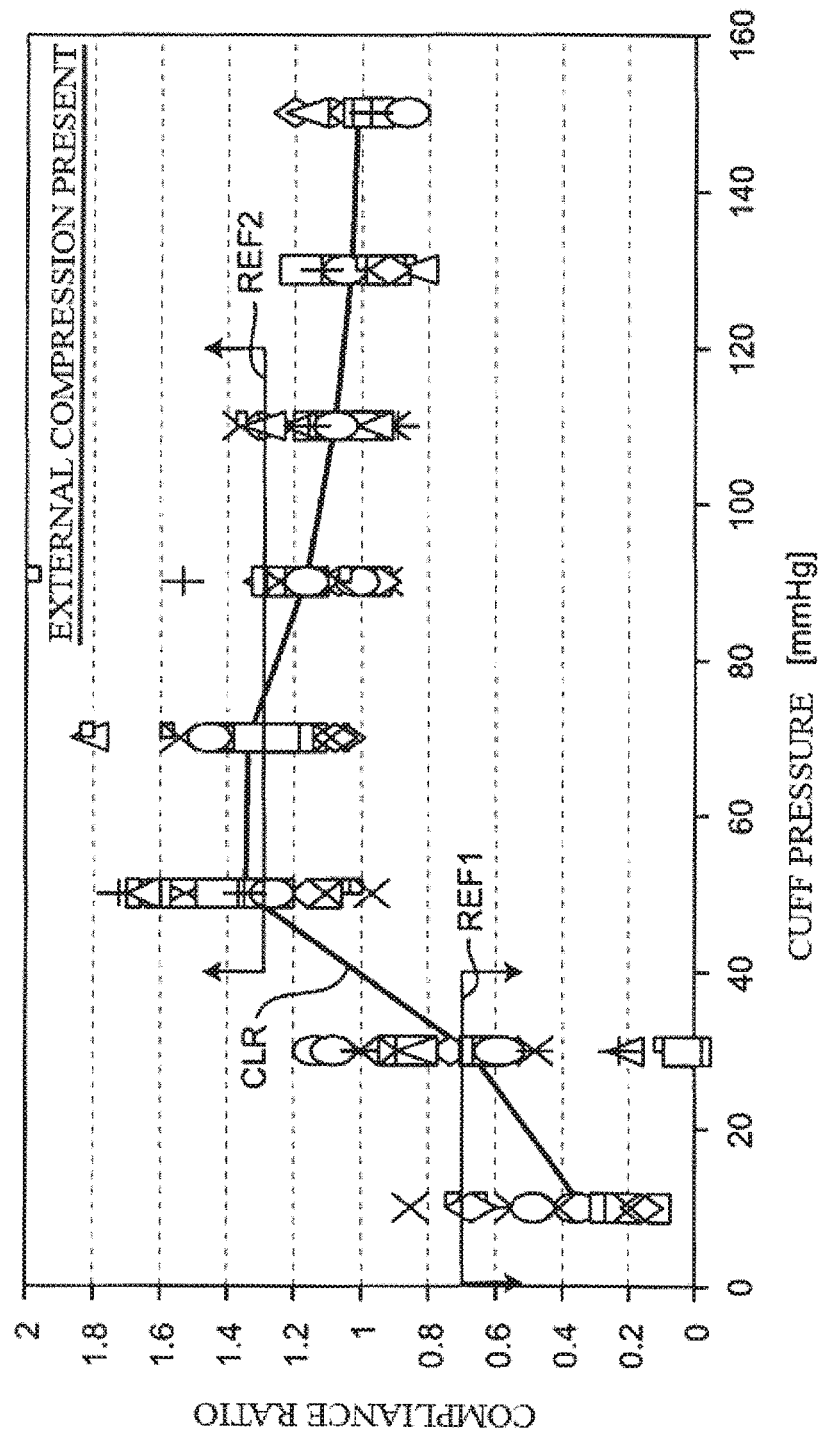
FIG. 14B is a diagram showing a change in the compliance ratio accompanying a change in the cuff pressure during blood pressure measurement (pressure increase process) in the case where there is external compression on the cuff (here, in the case where the cuff is placed under the torso of the measurement subject).

FIG. 14A shows change in a compliance ratio accompanying change in the cuff pressure during blood pressure measurement (pressure increase process) in the case where there is no external compression on the cuff 20. On the other hand, FIG. 14B shows change in a cuff compliance ratio accompanying change in the cuff pressure during blood pressure measurement (pressure increase process) in the case where there is external compression on the cuff 20 (here, a case in which the cuff 20 is placed under the torso of the measurement subject 90). Here, "compliance ratio" means the ratio between the cuff compliance calculated during blood pressure measurement and the cuff compliance (referred to as "reference cuff compliance") measured once as a reference in a state in which there is no external compression on the cuff 20. In other words, (compliance ratio)=(cuff compliance measured during blood pressure measurement)/(reference cuff compliance). Thus, the compliance ratio is used to more accurately determine whether or not there is external compression on the cuff 20. In FIGS. 14A and 14B, the data of the compliance ratio during multiple instances of blood pressure measurement is denoted by respective signs at the locations of cuff pressures 10 mmHg, 30 mmHg, 50 mmHg, 70 mmHg, 90 mmHg, 110 mmHg, 130 mmHg, 150 mmHg, . . . . Also, the average values of the data of the multiple instances are denoted as a line graph CLR.

As can be understood from FIG. 14A, if there is no external compression on the cuff 20, the compliance ratio is approximately constant (except for the location of the cuff pressure 10 mmHg in the low pressure region). On the other hand, as can be understood from FIG. 14B, if there is external compression on the cuff 20, the compliance ratio (graph CLR) has a maximum value in the intermediate pressure region (40 mmHg or more and 120 mmHg or less) in the pressure increase process. Also, as can be understood from FIGS. 14A and 14B, in both the case where there is no external compression on the cuff 20 and the case where there is external compression, there is significant variation in the compliance ratio in the low pressure region (0 mmHg to less than 40 mmHg). This is thought to be because the volume of the cuff 20 tends to not increase in some cases due not only to external compression but also to variation in the tensile force of wrapping the cuff 20 around the measurement site.

In view of this, in this example, taking these circumstances into consideration, it is determined that there is external compression on the cuff 20 only if, in the pressure increase process, the compliance ratio (CLR) is less than a first threshold REF1 (in this example, 0.7) in the low pressure region (0 mmHg to less than 40 mmHg) and the compliance ratio CLR is greater than or equal to a second threshold REF2 (in this example, 1.3) in the intermediate pressure region (40 mmHg or more and 120 mmHg or less). It is determined that there is no external compression in other cases, that is, if, in the pressure increase process, the compliance ratio CLR is greater than or equal to the first threshold REF1 (=0.7) in the low pressure region (0 mmHg to less than 40 mmHg), or the compliance ratio CLR is less than the second threshold REF2 (=1.3) in the intermediate pressure region (40 mmHg or more and 120 mmHg or less). Since REF1<REF2, this determination condition matches the condition of whether or not the compliance ratio has a maximum value in the intermediate pressure region (40 mmHg or more and 120 mmHg or less).

Figure 11:
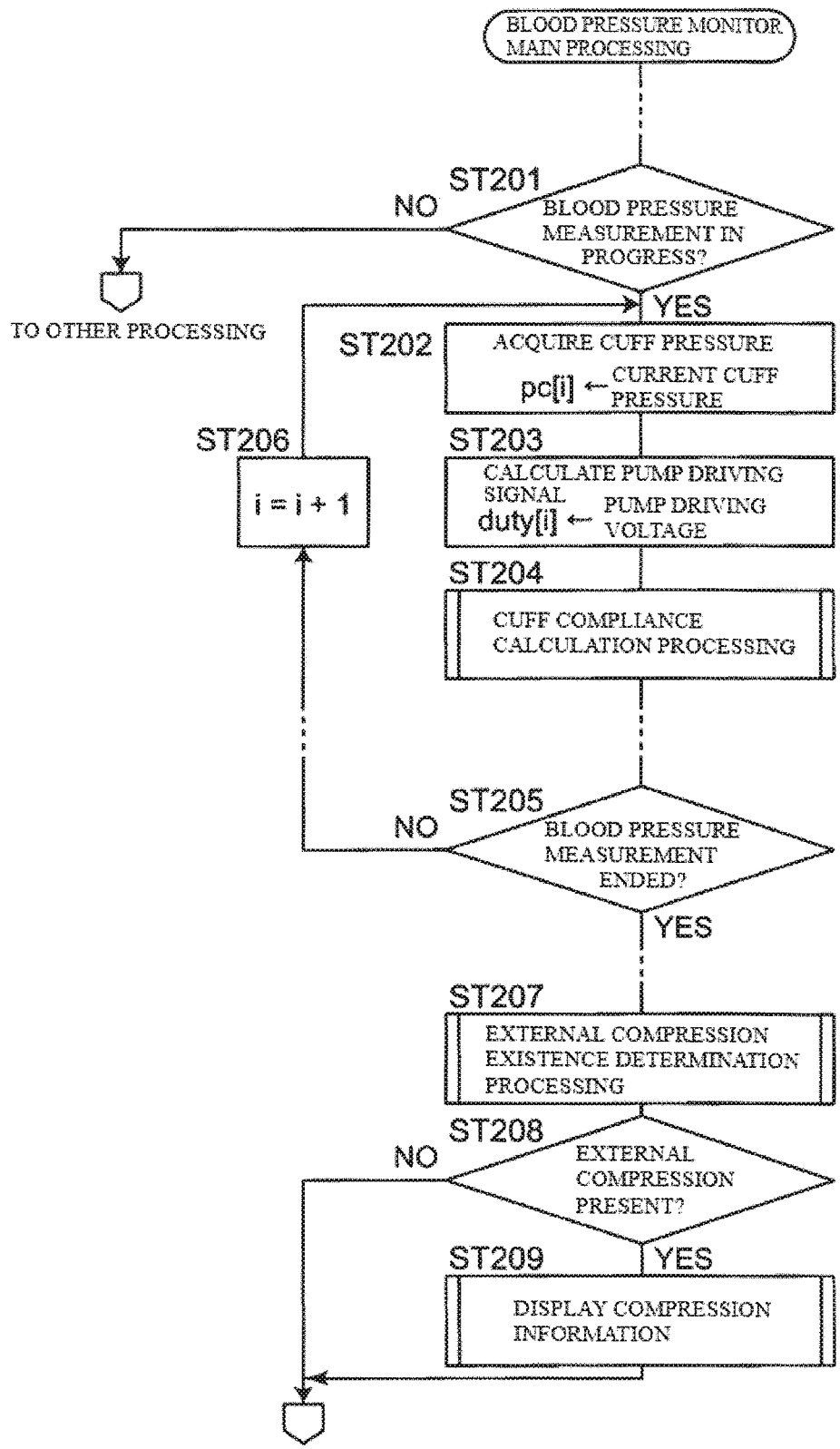
FIG. 11 is a diagram showing portions of the overall operation flow (portions relating to detection of external compression) of FIG. 5.
Figure 12:
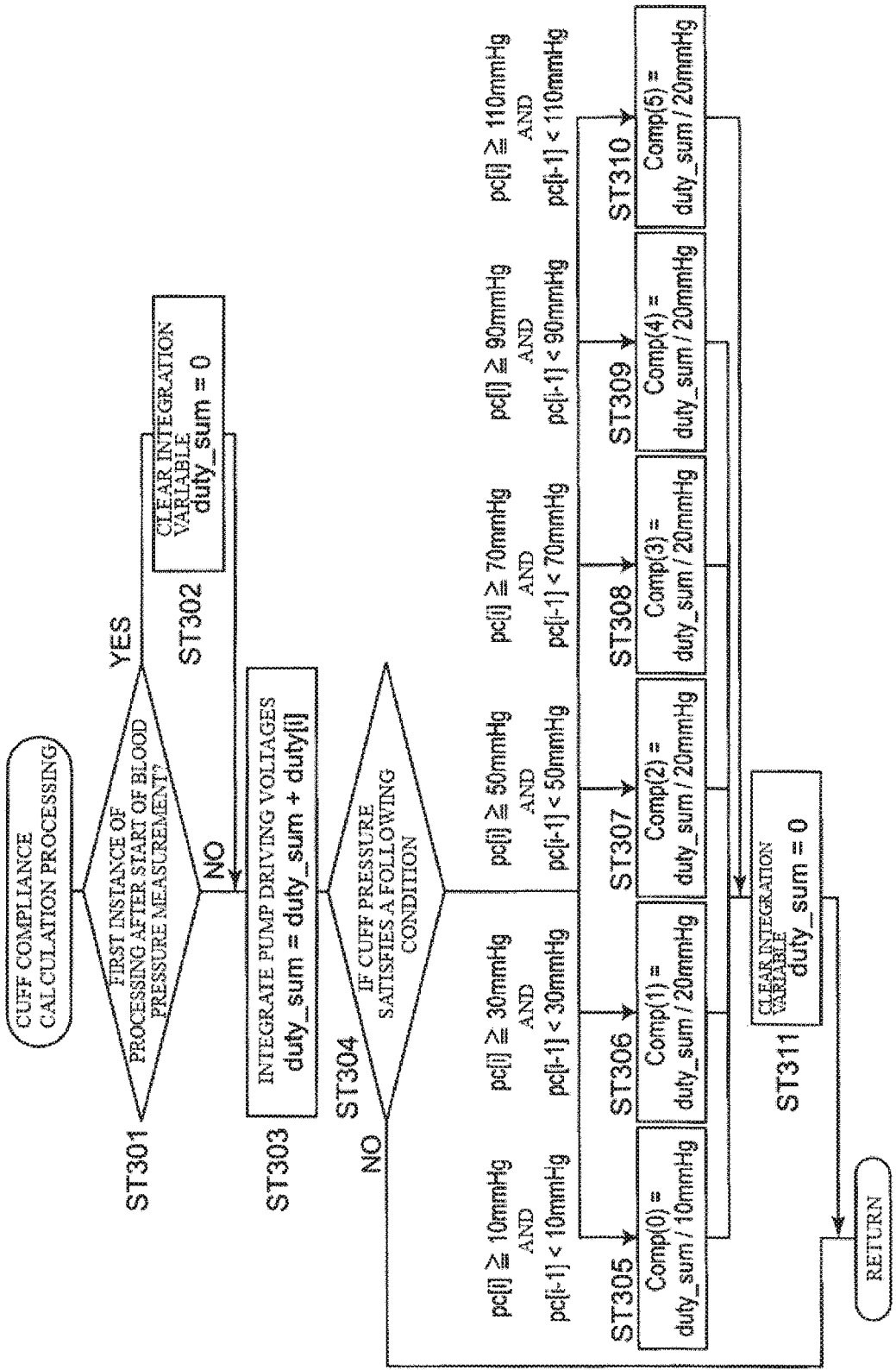
FIG. 12 is a diagram showing a specific flow of cuff compliance calculation processing shown in FIG. 11.
Figure 13:
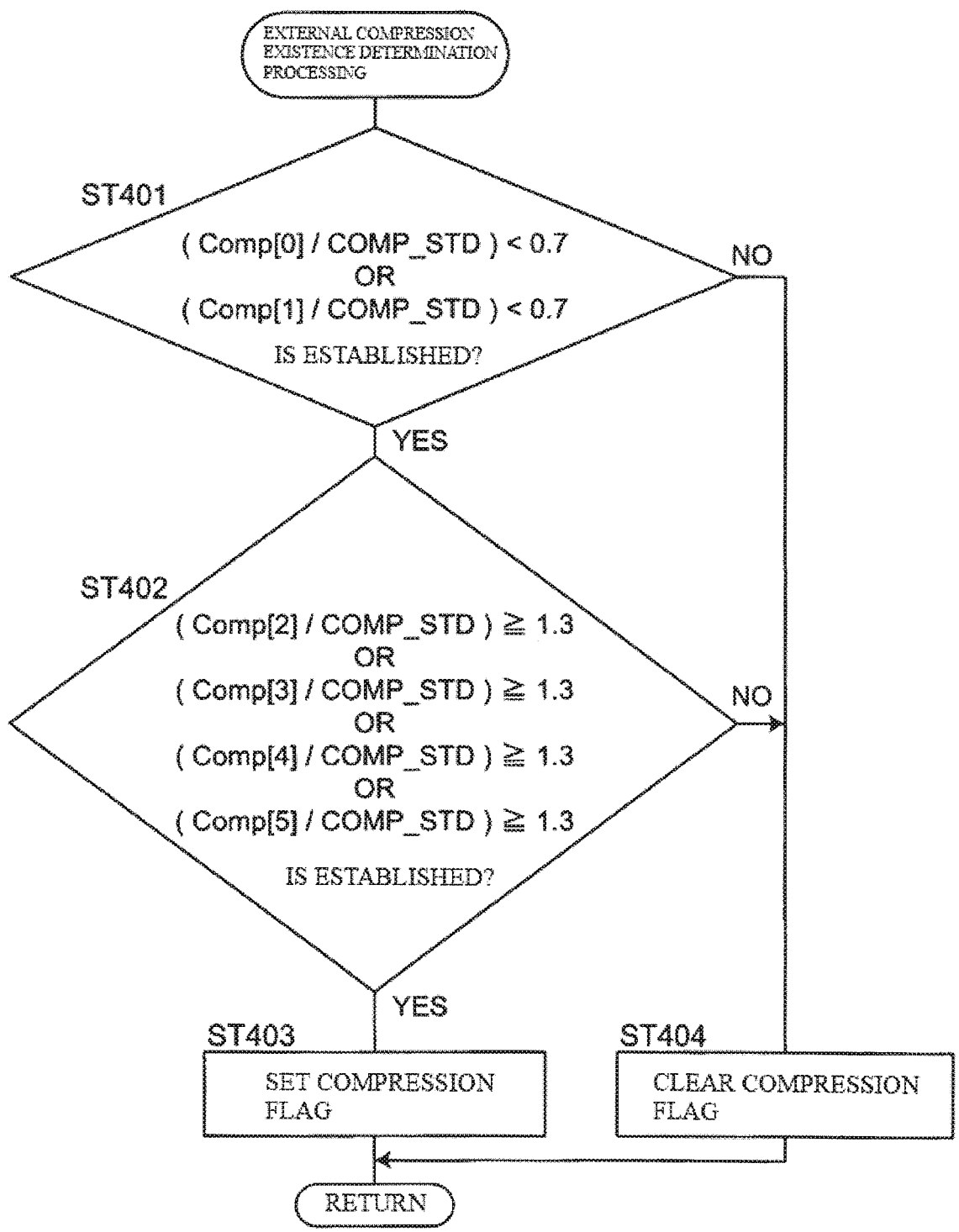
FIG. 13 is a diagram showing a specific flow of cuff pressure existence detection processing shown in FIG. 11.

In order to determine whether or not there is external compression based on this determination condition, the CPU 100 functions as an external compression detection unit and executes the operation flow shown in FIGS. 11 to 13.

FIG. 11 shows portions of the overall operation flow (portions related to detection of external compression) in FIG. 5. That is, if blood pressure measurement is in progress (YES in step ST201 of FIG. 11), the cuff pressure is acquired and the current cuff pressure is set as pc[i] (step ST202). Here, i is an index indicating the number of instances of processing, and in the first instance, i=0. Next, calculation for a pump driving signal (duty) is performed, and the current pump driving voltage is set as duty[i] (step ST203). Next, cuff compliance calculation processing (FIG. 12) for obtaining a cuff compliance is performed (step ST204).

As shown in FIG. 12, in the cuff compliance calculation processing, if it is the first instance of processing after the start of blood pressure measurement (the start of pressure increase) (YES in step ST301 of FIG. 12), an integration variable duty_sum for indicating an integration value (integration value) of the pump driving voltage is cleared (set to duty_sum=0) (step ST302). Next, the current pump driving voltage duty[i] is added to the integration variable duty_sum (step ST303). If the current cuff pressure pc[i] has not reached a predetermined value (10 mmHg at first) (NO in step ST304), the processing returns to the flow of FIG. 11 (NO in step ST205). Also, the index i indicating the number of instances of processing is incremented (increased by one) in step ST206 of FIG. 11, and the processing of steps ST202 and ST203 and steps ST301 to ST303 in FIG. 12 is repeated. When the current cuff pressure pc reaches 10 mmHg in step ST304 (when pc[i]≥10 mmHg and pc[i−1]<10 mmHg), the cuff compliance at the cuff pressure 10 mmHg is obtained as Comp(0)=duty_sum/10 mmHg (step ST305). Then, the addition variable duty_sum is cleared, and the processing returns to the flow of FIG. 11 (NO in step ST205). Then, the index i indicating the number of instances of processing is incremented in step ST206 of FIG. 11, and the processing of steps ST202 and ST203 and steps ST301 to ST303 of FIG. 12 is repeated. Then, when the current cuff pressure pc[i] reaches 30 mmHg in step ST304 (when pc[i]≥30 mmHg and pc[i−1]<30 mmHg), the cuff compliance at the cuff pressure 30 mmHg is obtained as Comp(1)=duty_sum/20 mmHg (step ST306). The processing is sequentially repeated in this manner, and when the current cuff pressure pc reaches 50 mmHg in step ST304 (when pc[i]≥50 mmHg and pc[i−1] <50 mmHg), the cuff compliance at the cuff pressure 50 mmHg is obtained as Comp(2)=duty_sum/20 mmHg (step ST307). Also, when the current cuff pressure pc reaches 70 mmHg in step ST304 (when pc[i]≥70 mmHg and pc[i−1] <70 mmHg), the cuff compliance at the cuff pressure 70 mmHg is obtained as Comp(3)=duty_sum/20 mmHg (step ST308). Also, when the current cuff pressure pc[i] reaches 90 mmHg in step ST304 (when pc[i]>90 mmHg and pc[i−1]<90 mmHg), the cuff compliance at the cuff pressure 90 mmHg is obtained as Comp(4)=duty_sum/20 mmHg (step ST309). Also, when the current cuff pressure pc[i] reaches 110 mmHg in step ST304 (when pc[i]≥110 mmHg and pc[i−1]<110 mmHg), the cuff compliance at the cuff pressure 110 mmHg is obtained as Comp(5)=duty_sum/20 mmHg (step ST310) Then, the addition variable duty_sum is cleared and the processing returns to the flow of FIG. 11.

If it is determined that the blood pressure measurement has ended in step ST205 of FIG. 11 (corresponds to step ST105 of FIG. 5) (YES in step ST205), external compression existence detection processing (FIG. 13) for determining whether or not there is external compression on the cuff 20 is performed (step ST207).

As shown in FIG. 13, in the external compression existence detection processing, an equation is used to determine whether or not the above-described determination condition has been satisfied. Note that for this determination, the CPU 100 functions in advance as a reference data acquisition unit, and in a state in which the cuff 20 is worn on a left upper arm 90a and there is no external compression, the CPU 100 increases the pressure in the cuff 20 and calculates the reference cuff compliance (reference signal COMP_STD) that is to serve as a reference at the times of the cuff pressures 10 mmHg, 30 mmHg, 50 mmHg, 70 mmHg, 90 mmHg, and 110 mmHg.

Also, it is determined that there is external pressure only in the case where, regarding the low pressure region (0 mmHg to less than 40 mmHg), $$\text{Comp}(0)/\text{COMP\_STD} < 0.7 \quad (\text{Eq.0})$$

or $$\text{Comp}(1)/\text{COMP\_STD} < 0.7 \quad (\text{Eq.1})$$

is established (YES in step S401) and, regarding the intermediate pressure region (40 mmHg or more and 120 mmHg or less), $$\text{Comp}(2)/\text{COMP\_STD} \geq 1.3 \quad (\text{Eq.2})$$

or $$\text{Comp}(3)/\text{COMP\_STD} \geq 1.3 \quad (\text{Eq.3})$$

or $$\text{Comp}(4)/\text{COMP\_STD} \geq 1.3 \quad (\text{Eq.4})$$

or $$\text{Comp}(5)/\text{COMP\_STD} \geq 1.3 \quad (\text{Eq.5})$$

is established (YES in step ST402). In this case, in step ST403, a compression flag indicating that there was external compression is set. Note that although COMP_STDs in Eq. 0 to Eq. 5 are indicated by the same reference signs for the sake of simplicity, they respectively indicate the reference cuff compliances at the times of the cuff pressures 10 mmHg, 30 mmHg, 50 mmHg, 70 mmHg, 90 mmHg, and 110 mmHg (the same applies also to Eq. 6 to Eq. 11, which will be described next).

On the other hand, it is determined that there is no external compression in the case where, regarding the low pressure region (0 mmHg to less than 40 mmHg), $$\text{Comp}(0)/\text{COMP\_STD} \geq 0.7 \quad (\text{Eq.6})$$

or $$\text{Comp}(1)/\text{COMP\_STD} \geq 0.7 \quad (\text{Eq.7})$$

is established (NO in step ST401), or, regarding the intermediate pressure region (40 mmHg or more and 120 mmHg or less), $$\text{Comp}(2)/\text{COMP\_STD} < 1.3 \quad (\text{Eq.8})$$

or $$\text{Comp}(3)/\text{COMP\_STD} < 1.3 \quad (\text{Eq.9})$$

or $$\text{Comp}(4)/\text{COMP\_STD} < 1.3 \quad (\text{Eq.10})$$

or $$\text{Comp}(5)/\text{COMP\_STD} < 1.3 \quad (\text{Eq.11})$$

is established (NO in step ST402). In this case, in step ST404, a no compression flag indicating that there was no external compression is set.

When the compression flag is set in step ST403, "1", which indicates that there is external compression in the current instance of blood pressure measurement, is stored in the "external compression" column of the above-described data table (Table 1). On the other hand, when the no compression flag is set in step ST404, "0", which indicates that there is no external compression in the current instance of blood pressure measurement, is stored in the "external compression" column of the data table (Table 1).

Thereafter, the processing returns to the flow of FIG. 11, and if there is external compression (YES in step ST208), compression information (e.g., the illustration J-2 shown in FIGS. 9A and 10B) indicating that there was external compression in the present instance of blood pressure measurement is displayed in step ST209 (corresponds to step ST110 of FIG. 5).

If it is determined whether or not there is external compression based on the above-described determination conditions in this way, it is possible to more accurately determine whether or not there is external compression on the cuff 20.

Example of Display on Hospital Terminal

Figure 3:
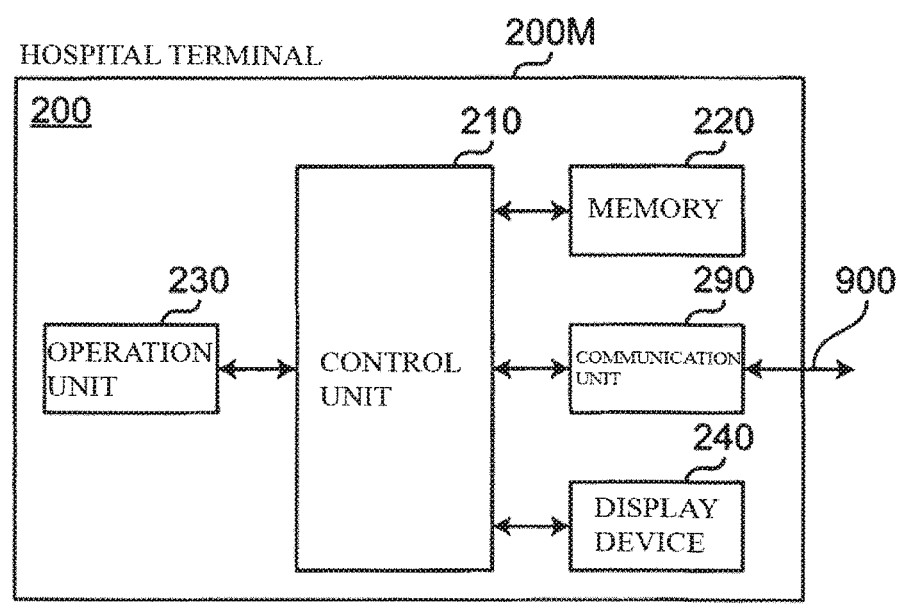
FIG. 3 is a diagram showing a block configuration of a hospital terminal that can communicate with the blood pressure monitor via a network.

FIG. 3 shows a block configuration of a hospital terminal 200 that can communicate with the blood pressure monitor 1 via a network 900. The hospital terminal 200 is composed of a commercially-available personal computer, includes a main body 200M, and includes a control unit 210 composed of a CPU, a memory 220 including a RAM (Random Access Memory) and a ROM (Read Only Memory), an operation unit 230 including a keyboard and a mouse, a display device 240 composed of an LCD, and a communication unit 290 for performing communication via the network 900, all of which are mounted in the main body 200M.

Figure 15:
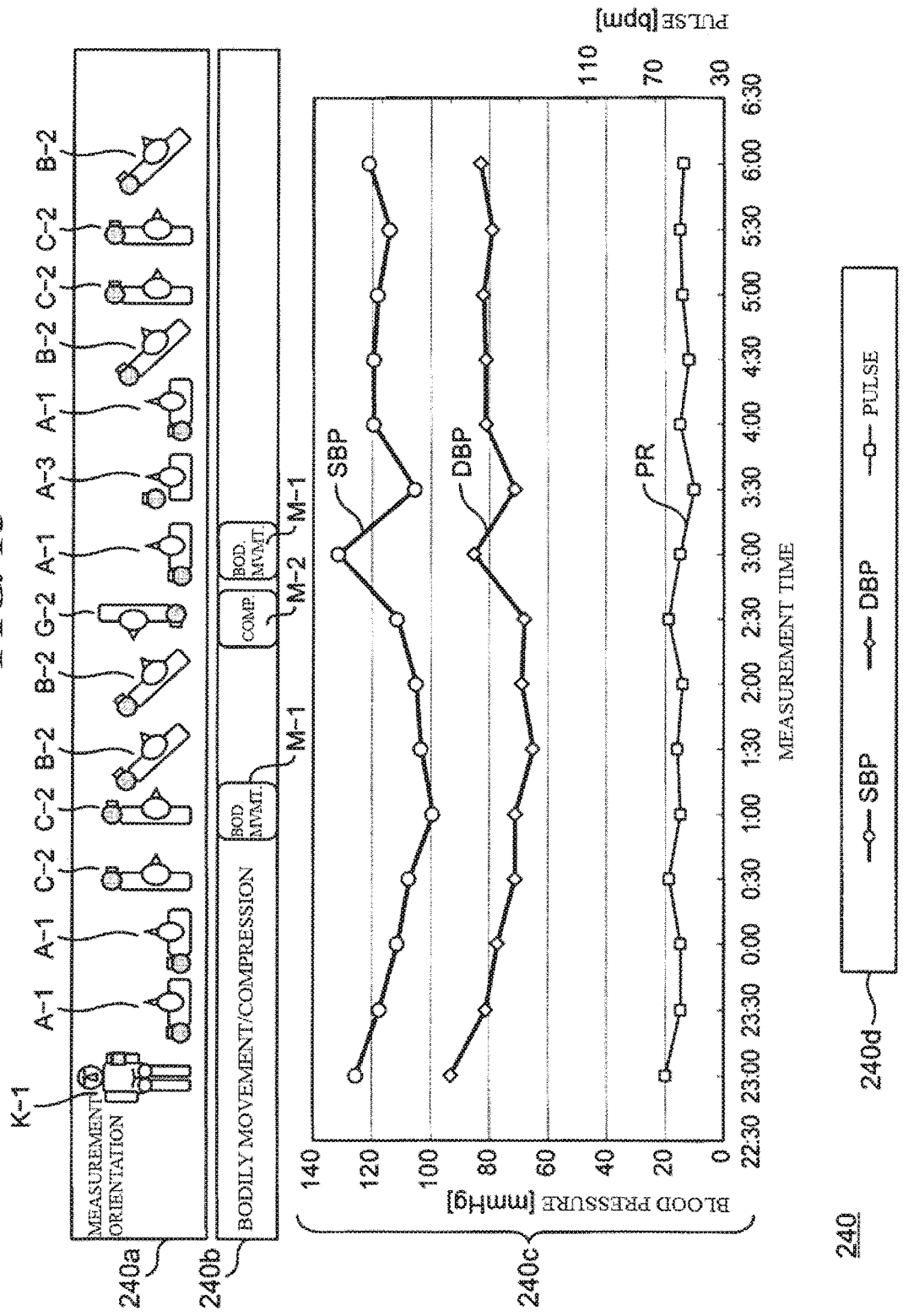
FIG. 15 is a diagram illustrating an image to be displayed on the display device of the hospital terminal.
Figure 16:
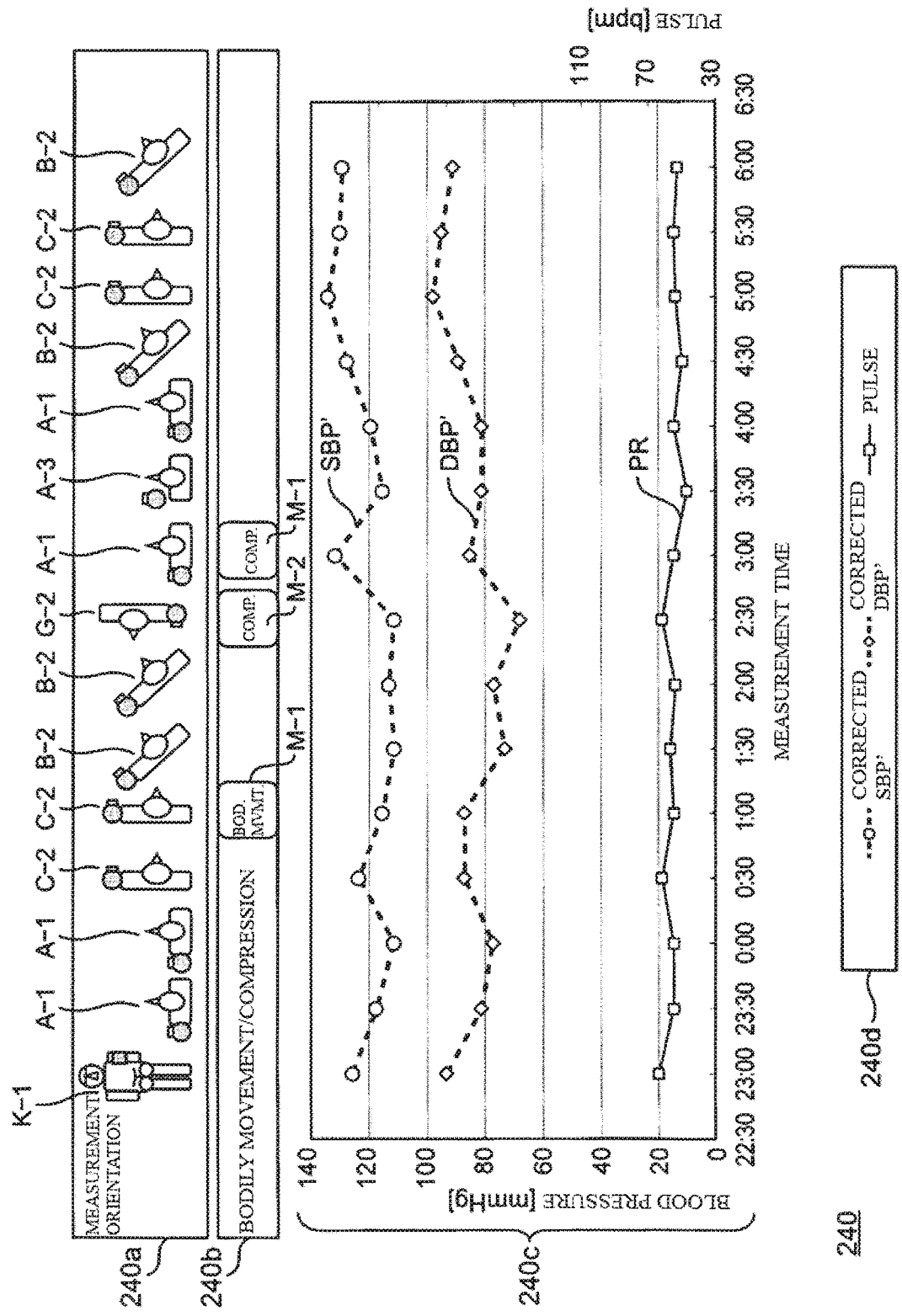
FIG. 16 is a diagram illustrating another image to be displayed on the display device of the hospital terminal.
Figure 17:
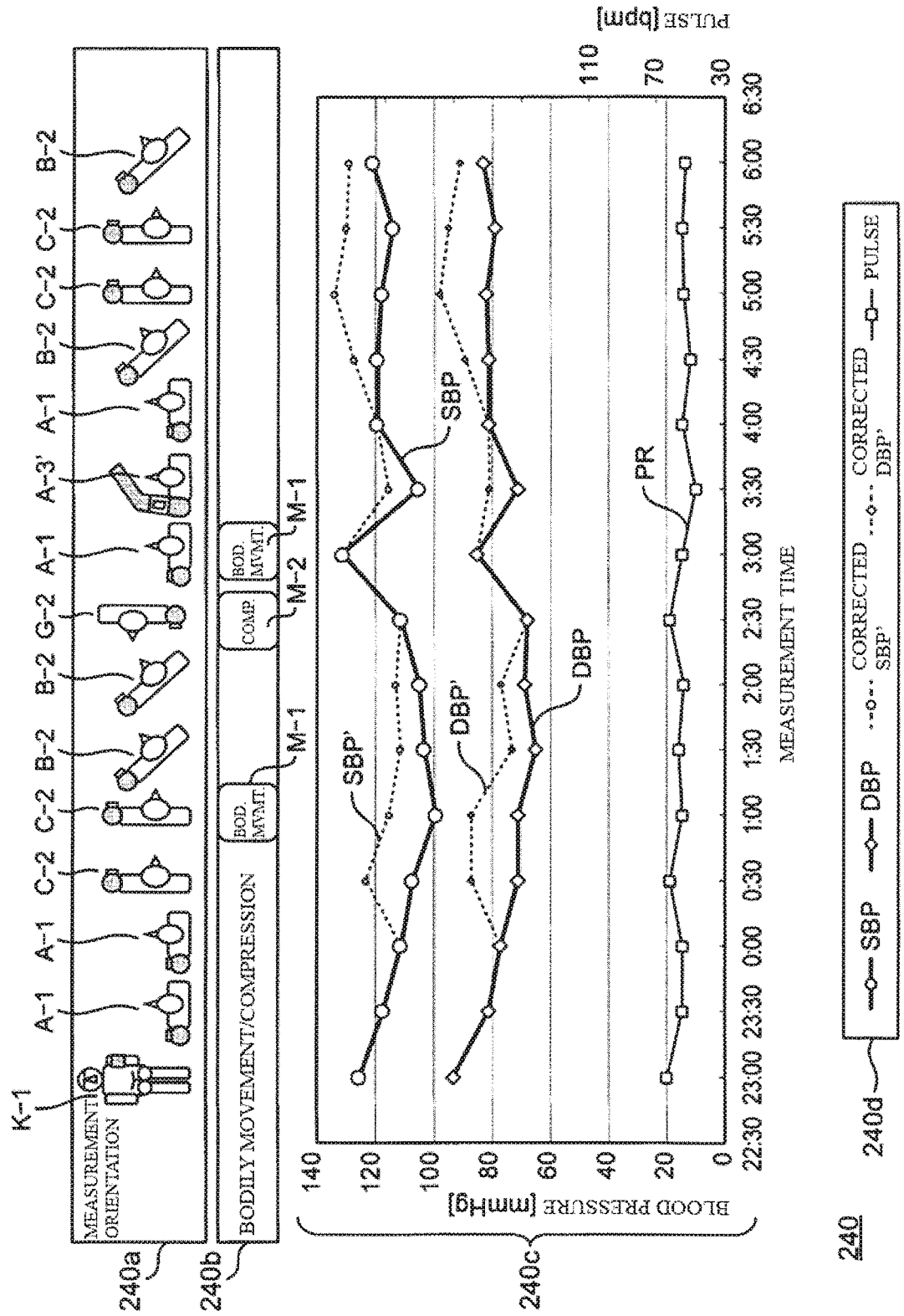
FIG. 17 is a diagram illustrating yet another image to be displayed on the display device of the hospital terminal.

FIGS. 15 to 17 illustrate images displayed on the display screen of the display device 240 based on the image data received by the hospital terminal 200 from the blood pressure monitor 1 via the communication unit 290.

For example, as shown in FIG. 15, the "measurement orientation" region 240a indicating the orientation of the measurement subject 90 during blood pressure measurement, the "bodily movement/compression" region 240b indicating whether or not there is bodily movement of the measurement subject 90 or compression, a blood pressure/pulse region 240c indicating the measured blood pressure values or the corrected blood pressure values, and a legend region 240d indicating a legend of reference signs displayed on the blood pressure/pulse region 240c are set on the display screen of the display device 240.

In the "measurement orientation" region 240a, the illustrations K-1, A-1, C-2, . . . , which correspond to the reference numerals "K-1", "A-1", "C-2", . . . stored in the above-described "orientation" column of the data table (Table 1) are displayed in alignment with the passage of time (measurement time shown on the horizontal axis in the blood pressure/pulse region 240c). By viewing the illustrations of the orientations displayed in the "measurement orientation" region 240a, a doctor serving as a user can intuitively understand the orientations of the measurement subject 90 during blood pressure measurement according to the passage of time. In the example shown in FIG. 15, it can be understood intuitively that the orientation of the measurement subject 90 changes from K-1 to A-1, A-1, C-2, C-2, B-2, B-2, G-2, A-1, A-3, A-1, B-2, C-2, C-2, and B-2 in the period of measurement times 23:00 to 6:00.

In the "bodily movement/compression" region 240b, the bodily movement information that is stored in the "bodily movement" column of the data table (Table 1) and indicates that there is bodily movement is indicated by a mark M-1 at the positions in the horizontal direction corresponding to the measurement times when there was bodily movement. In addition, the compression information that is stored in the "external compression" column of the data table (Table 1) and indicates that there is external compression is indicated by a mark M-2 at the position on the horizontal axis corresponding to the measurement time when there was external compression. The mark M-1 is constituted by the words "BOD. MVMT." being included in a rectangle with rounded corners. The mark M-2 is constituted by the word "COMP." being included in a rectangle with rounded corners. By viewing the marks M-1 and M-2 displayed in the "bodily movement/compression" region 240b, a doctor serving as a user can intuitively understand that there was bodily movement of the measurement subject 90 and that there was external compression on the cuff 20 at a specific blood pressure measurement time. In the example shown in FIG. 15, it can be understood intuitively that there was bodily movement during blood pressure measurement at the blood pressure measurement times 1:00 and 3:00, and that there was external compression during blood pressure measurement at the blood pressure measurement time 2:30.

In the blood pressure/pulse region 240c, the measured blood pressure values (systolic blood pressure SBP and diastolic blood pressure DBP) in the data table (Table 1) and the pulse value PR stored in the "pulse" column are displayed as line graphs in this example. By viewing these line graphs, a user can intuitively understand the passage of time of the blood pressure values and the pulse of the measurement subject 90. Also, by viewing both the illustrations of the orientations displayed in the "measurement orientation" region 240a and the line graph of the blood pressure values displayed in the blood pressure/pulse region 240c, the user can intuitively understand the influence that the orientation, bodily movement, and external compression have on the blood pressure value of the measurement subject 90.

Accordingly, for example, in the case of diagnosing the health state of the measurement subject 90, a doctor serving as a user can make a diagnosis giving consideration to the influence that the orientation, bodily movement, and external compression have on the blood pressure value of the measurement subject 90. Specifically, for example, if the orientation has a large influence on the blood pressure value of the measurement subject 90, the doctor can make a diagnosis based only on the blood pressure values measured at times when the measurement subject 90 was in a specific orientation (e.g., A-1). Also, if the bodily movement or the external compression has a large influence on the blood pressure value of the measurement subject 90, it is possible to ignore the blood pressure values measured when there is bodily movement and the blood pressure values measured when there is external compression, and to make a diagnosis based only on the blood pressure values measured when there is no bodily movement and no external compression.

As shown in FIG. 16, in the blood pressure/pulse region 240c, the corrected blood pressure values (systolic blood pressure SBP' and diastolic blood pressure DBP') in the data table (Table 1) may be displayed as line graphs instead of the measured blood pressure values (systolic blood pressure SBP and diastolic blood pressure DBP) in the data table (Table 1). Accordingly, by viewing both the illustrations of the orientations displayed in the "measurement orientation" region 240a and the line graph of the corrected blood pressure values displayed in the blood pressure/pulse region 240c, a doctor serving as a user can intuitively understand whether or not the blood pressure values of the measurement subject 90 have been appropriately corrected according to the orientations of the measurement subject 90 during blood pressure measurement.

Also, as shown in FIG. 17, the corrected blood pressure values (systolic blood pressure SBP' and diastolic blood pressure DBP') in the data table (Table 1) may be displayed along with the measured blood pressure values (systolic blood pressure SBP and diastolic blood pressure DBP) in the data table (Table 1) as line graphs in the blood pressure/pulse region 240c. Accordingly, by viewing the illustrations of the orientations displayed in the "measurement orientation" region 240a and the line graphs of the uncorrected and corrected blood pressure values displayed in the blood pressure/pulse region 240c, a doctor serving as a user can more intuitively understand whether or not the blood pressure values of the measurement subject 90 were corrected appropriately according to the orientation of the measurement subject 90 during blood pressure measurement.

Modified Examples

In the example above, as shown in FIGS. 8A to 8H, the orientations of the measurement subject 90 are detected as combinations of eight types of "torso angles" and four or three types of "arm positions". Furthermore, in correspondence to this, the orientations of the measurement subject 90 are indicated using the illustrations A-1 to A-4, B-1 to B-4, C-1 to C-4, D-1 to D-4, E-1 to E-3, F-1 to F-3, G-1 to G-3, and H-1 to H-3, which are obtained by combining eight types of torso patterns and four or three types of arm patterns. However, there is no limitation to this, and for example, the torso angle may be detected roughly as four types, namely 0 degrees (supine position), 90 degrees (right side position), 180 degrees (prone position), and 270 degrees (left side position), and in correspondence to this, the torso angle may be displayed as four types of torso patterns.

Also, the "arm position" of the measurement subject 90 may be at a special arm position other than the four or three types of representative "arm positions" in FIGS. 8A to 8H. In this case, it is desirable that with regard to this special arm position, the points that are to be detected in the XZ coordinate plane in the third rows in FIGS. 8A to 8H and in the XY coordinate plane in the fourth rows are defined, and the arm pattern that indicates the special arm position is prepared. For example, as shown in the "measurement orientation" region 240a, at the measurement time 3:30 shown in FIG. 17, the torso angle of the measurement subject 90 is 0 degrees (supine position). In this case, the left upper arm 90a is in an arm position of being separated frontward with respect to the torso 90b of the measurement subject 90 (being extended approximately vertically upward). In response to this, it is desirable that the points that are to be detected in the XZ coordinate plane in the third row and in the XY coordinate plane in the fourth row in FIG. 8A are defined and the arm pattern indicating this arm position (in this example, illustration A-3') is prepared.

Also, in the example above, the orientation of the measurement subject 90 is indicated using the illustrations A-1 to A-4, B-1 to B-4, C-1 to C-4, D-1 to D-4, E-1 to E-3, F-1 to F-3, G-1 to G-3, and H-1 to H-3 in the first rows (top rows) of FIGS. 8A to 8H. However, there is no limitation to this, and the orientation of the measurement subject 90 may be indicated using illustrations of another type, for example, the illustrations in the second rows of FIGS. 8A to 8H. The illustrations in the second rows in FIGS. 8A to 8H indicate schematic views of the orientations of the measurement subject 90 from above in the vertical direction. In the illustrations shown in the second rows, the head 90*h* of the measurement subject 90 is indicated by an oval, the torso 90*b* is indicated by a half-oval, and the left upper arm 90*a* is indicated by a rounded-corner rectangle. With this kind of illustration as well, the user can intuitively understand the orientations of the measurement subject 90 during blood pressure measurement according to the passage of time.

Also, with the blood pressure monitor 1, the cuff 20 and the main body 10 are constituted integrally, but there is no limitation to this. Instead, the cuff 20 and the main body 10 may be constituted separately, and may be connected via an elongated tube corresponding to the air tube 39. In this case, the acceleration sensor 34 is preferably mounted in (built in) the cuff 20 so as to be able to detect the orientation of the measurement subject 90.

As is described above, the electronic blood pressure monitor of this disclosure includes:

a blood pressure measurement cuff configured to be worn on a measurement site of a measurement subject;

a blood pressure measurement unit configured to measure a blood pressure value of the measurement subject using the cuff; and an external compression detection unit configured to detect whether or not there was external compression on the cuff during the blood pressure measurement performed by the blood pressure measurement unit, wherein in each predetermined pressure segment, the external compression detection unit calculates a cuff compliance, which is an amount of air that is to be pumped into the cuff and is needed to increase pressure in the cuff per unit pressure, as the pressure of the cuff is increased by the blood pressure measurement unit during blood pressure measurement, and the external compression detection unit determines whether or not there is external compression on the cuff based on a change indicated by the cuff compliance in each pressure segment.

In the present specification, "during blood pressure measurement" does not indicate the entire period in which the blood pressure measurement cuff is worn for night-time blood pressure measurement and the like, for example, but indicates a timing during which the blood pressure values of the measurement subject are measured by actually increasing or reducing the pressure of the above-described blood pressure measurement cuff.

Also, "external compression" indicates compression from the outside of the external circumferential surface of the blood pressure monitor that is wrapped around the measurement site. In other words, "external compression" does not encompass compression from the measurement site (inner circumferential surface side of the cuff) around which the blood pressure measurement cuff is wrapped. Typically, external compression occurs when the measurement subject lying on the bed surface places the cuff worn on the measurement site under the torso in the case of night-time blood pressure measurement. Note that "bed surface" widely indicates a surface on which a measurement subject can lie, such as an upper surface of a bed or futon. The torso of the measurement subject may be wearing clothes.

With the electronic blood pressure monitor of the present disclosure, in a state in which the cuff is worn on the measurement site of the measurement subject, a fluid is supplied to the cuff to increase the pressure, and thereby the measurement site is compressed, and the blood pressure measurement unit performs blood pressure measurement. According to this, the blood pressure value is obtained. Also, the external compression detection unit detects whether or not there was external compression on the cuff during the blood pressure measurement performed by the blood pressure measurement unit. Accordingly, the user can check whether or not there was external compression on the cuff during blood pressure measurement, based on the detection result. Moreover, in each predetermined pressure segment, the external compression detection unit calculates a cuff compliance, which is an amount of air that is to be pumped into the cuff and is needed to increase pressure in the cuff per unit pressure, as the pressure of the cuff is increased by the blood pressure measurement unit during blood pressure measurement, and the external compression detection unit determines whether or not there is external compression on the cuff based on a change indicated by the cuff compliance in each pressure segment. Accordingly, for example, if the cuff is wrapped tightly around the measurement site, it is possible to avoid a circumstance in which it is erroneously determined that there is external compression on the cuff due to the influence of the tension of the wrapping. Accordingly, it is possible to more accurately determine whether or not there is external compression on the cuff.

With an electronic blood pressure monitor of an embodiment, the external compression detection unit determines whether or not there is external compression on the cuff according to whether or not the cuff compliance has a maximum value with respect to pressure change of the cuff in an intermediate pressure region in which the pressure of the cuff is 40 mmHg or more and 120 mmHg or less.

In the present specification, "cuff compliance" means the amount of air that is to be pumped into the cuff, and which is needed to increase the pressure, per unit pressure of the cuff. For example, milliliters/millimeters of mercury (ml/mmHg) are used as the units.

Also, the "intermediate pressure region" (40 mmHg or more and 120 mmHg or less) is a pressure region that is set based on experiments performed by the inventor of the present invention.

In general, if there is no external compression on the cuff, the cuff compliance gradually decreases and is saturated as the fluid is supplied to the cuff and the pressure is increased from the low pressure region (0 mmHg to less than 40 mmHg) to the high pressure region (more than 120 mmHg). The reason for this is as follows: the volume of the cuff easily increases in the low pressure region, and therefore a large amount of air is needed to increase the cuff pressure, but if the tensile force of the cuff increases due to the cuff pressure increasing by a certain extent, the volume of the cuff substantially stops increasing. On the other hand, if the measurement subject lying on the bed surface places the cuff worn on the measurement site under his or her torso, the cuff is compressed from the outside (the torso and the bed surface). In this case, in the low pressure region (0 mmHg to less than 40 mmHg), the volume of the cuff increases due to the cuff pressing back against the torso of the measurement subject. Accordingly, the cuff compliance changes gradually from a low value (varies due to the influence of the tensile force of wrapping the cuff around the measurement site) to a high value. On the other hand, in the high pressure region (more than 120 mmHg), the torso is pressed by the upper portion of the cuff due to the inflation of the cuff, and therefore, similarly to the case in which there is no external compression, the cuff compliance gradually decreases and is saturated. As a result, in the intermediate range (40 mmHg or more, 120 mmHg or less), the cuff compliance has a maximum value accompanying the increase of the cuff pressure. In view of this, with the electronic blood pressure monitor of this embodiment, the external compression detection unit determines whether or not there is external compression on the cuff according to whether or not the cuff compliance has a maximum value with respect to the pressure change of the cuff in the intermediate pressure region (40 mmHg or more and 120 mmHg or less). Accordingly, it is possible to accurately determine whether or not there is external compression on the cuff.

An electronic blood pressure monitor of an embodiment includes a reference data acquisition unit configured to increase pressure in the cuff and calculate a reference cuff compliance that is to serve as a reference, in a state in which the cuff is worn on the measurement site and there is no external compression, wherein the external compression detection unit detects a compliance ratio between the cuff compliance calculated during blood pressure measurement and the reference cuff compliance, and the external compression detection unit detects whether or not there is external compression on the cuff according to whether or not the compliance ratio has a maximum value with respect to the pressure change of the cuff in an intermediate pressure region in which the pressure of the cuff is 40 mmHg or more and 120 mmHg or less.

In the present specification, "compliance ratio" means (cuff compliance calculated during blood pressure measurement)/(reference cuff compliance).

With the electronic blood pressure monitor of this embodiment, the pressure is increased and the reference data acquisition unit calculates the reference cuff compliance that is to serve as a reference in a state in which the cuff is worn on the measurement site and there is no external compression. The external compression detection unit detects the compliance ratio between the cuff compliance calculated during blood pressure measurement and the reference cuff compliance. Furthermore, the external compression detection unit detects whether or not there is external compression on the cuff according to whether or not the compliance ratio has a maximum value in the pressure change of the cuff in the intermediate pressure region, in which the pressure of the cuff is 40 mmHg or more and 120 mmHg or less. Accordingly, it is possible to more accurately determine whether or not there is external compression on the cuff.

With an electronic blood pressure monitor of an embodiment, the external compression detection unit determines that there is external compression on the cuff only when the compliance ratio is smaller than a predetermined threshold in a low pressure region in which the pressure of the cuff is less than 40 mmHg.

In the low pressure region, in which the pressure of the cuff is less than 40 mmHg, the volume of the cuff tends to not increase in some cases due not only to external compression but also to variation in the tensile force of wrapping the cuff around the measurement site. In this case, there is a possibility that it will be erroneously determined that there is external compression on the cuff. In view of this, with the electronic blood pressure monitor of this embodiment, the external compression detection unit determines that there is external compression on the cuff only when the compliance ratio is smaller than a predetermined threshold in a low pressure region in which the pressure of the cuff is less than 40 mmHg. Accordingly, if the cuff is wrapped tightly around the measurement site, it is possible to avoid a situation in which it is erroneously determined that there is external compression on the cuff due to the influence of the tensile force of the wrapping. Accordingly, it is possible to more accurately determine whether or not there is external compression on the cuff.

An electronic blood pressure monitor of an embodiment includes a storage unit configured to store compression information indicating a result of detection performed by the external compression detection unit, in association with the blood pressure value measured by the blood pressure measurement unit.

With the blood pressure monitor of this embodiment, the storage unit stores the compression information indicating the result of detection performed by the external compression detection unit, in association with the blood pressure value measured by the blood pressure measurement unit. The storage content of the storage unit is read out, whereby the user can check whether or not there was external compression on the cuff during blood pressure measurement.

An electronic blood pressure monitor of an embodiment includes a notification unit configured to perform notification of compression information indicating the result of detection performed by the external compression detection unit, in association with the blood pressure value measured by the blood pressure measurement unit.

With the blood pressure monitor of this embodiment, the notification unit performs notification of the compression information indicating the result of detection performed by the external compression detection unit, in association with the blood pressure value measured by the blood pressure measurement unit. According to the notification content of the notification unit, the user can find out whether or not there was external compression on the cuff during blood pressure measurement. Accordingly, for example, in the case of diagnosing the health state of the measurement subject, a doctor serving as a user can make a diagnosis giving consideration to the influence that the external compression has on the blood pressure value of the measurement subject. Specifically, for example, if the external compression has a large influence on the blood pressure values of the measurement subject 90, the blood pressure values measured when there was external compression can be ignored, and diagnosis can be performed based on only the blood pressure values measured when there was no external compression.

Also, an electronic blood pressure monitor of an embodiment includes a reference data acquisition unit configured to increase pressure in the cuff and calculate a reference cuff compliance that is to serve as a reference, in a state in which the cuff is worn on the measurement site and there is no external compression, wherein the external compression detection unit detects a compliance ratio between the cuff compliance calculated during blood pressure measurement and the reference cuff compliance, and the external compression detection unit detects whether or not there is external compression on the cuff according to whether or not the compliance ratio is smaller than a predetermined first threshold in a low pressure region in which the pressure of the cuff is less than 40 mmHg and the compliance ratio is greater than or equal to a predetermined second threshold in an intermediate pressure region in which the pressure of the cuff is 40 mmHg or more and 120 mmHg or less.

As is clear from the foregoing description, with the electronic blood pressure monitor of the present disclosure, a user can check whether or not there was external compression on a cuff during blood pressure measurement.

The above-described embodiments are exemplary and various modifications are possible without departing from the scope of the invention. The above-described multiple embodiments can be established separately, but combinations of the embodiments are also possible. Also, the various characteristics of the different embodiments can be established separately, but combinations of the characteristics in the different embodiments are also possible.

The invention claimed is:

1. An electronic blood pressure monitor, comprising:
a cuff for blood pressure measurement configured to be worn on a measurement site of a measurement subject;
a display; and a programmed processor,
wherein
the programmed processor operates as a reference data acquisition unit to increase pressure in the cuff and calculate a reference cuff compliance that is to serve as a reference, in a state in which the cuff is worn on the measurement site and there is no external compression,
the programmed processor operates as a blood pressure measurement unit to measure a blood pressure value of the measurement subject using the cuff,
the programmed processor operates as an external compression detection unit to detect whether or not there was external compression on the cuff during a blood pressure measurement performed by the programmed processor operator as the blood pressure measurement unit,
when operating as the external compression detection unit, the programmed processor calculates cuff compliances, each of which is an amount of air that is to be pumped into the cuff and is needed to increase pressure in the cuff per unit pressure, in every one of a plurality of pressure intervals that each has a predetermined range of pressure in a pressure increase process of the cuff during the blood pressure measurement,
the programmed processor calculates a compliance ratio between each cuff compliance calculated during the blood pressure measurement and the reference cuff compliance,
the programmed processor determines whether or not there is external compression on the cuff according to whether or not the cuff compliance ratios have a peak in a second pressure region in which the pressure of the cuff is 40 mmHg or more and 120 mmHg or less, and
the programmed processor operates as a notification unit to output, to the display, compression information that indicates a result of determining whether or not there is external compression in correspondence with the blood pressure value, and the display is controlled by the programmed processor to display the compression information in correspondence with the blood pressure value on a display screen.

2. The electronic blood pressure monitor according to claim 1,
wherein, when operating as the external compression detection unit, the programmed processor determines that there is external compression on the cuff only when the compliance ratios have a peak in the second pressure region and when the compliance ratios in a first pressure region, in which the pressure of the cuff is 0 mmHg or more and less than 40 mmHg, are smaller than a predetermined threshold in the pressure increase process of the cuff.

3. The electronic blood pressure monitor according to claim 1, further comprising:
a storage unit including a memory and configured to store the compression information in correspondence with the blood pressure value.

4. An electronic blood pressure monitor, comprising:
a cuff for blood pressure measurement configured to be worn on a measurement site of a measurement subject;
a display; and a programmed processor, wherein
the programmed processor operates as a reference data acquisition unit to increase pressure in the cuff and calculate a reference cuff compliance that is to serve as a reference, in a state in which the cuff is worn on the measurement site and there is no external compression,
the programmed processor operates as a blood pressure measurement unit to measure a blood pressure value of the measurement subject using the cuff,
the programmed processor operates as an external compression detection unit to detect whether or not there was external compression on the cuff during a blood pressure measurement performed by the programmed processor operating as the blood pressure measurement unit,
when operating as the external compression detection unit, the programmed processor calculates cuff compliances, each of which is an amount of air that is to be pumped into the cuff and is needed to increase pressure in the cuff per unit pressure, in every one of a plurality of pressure intervals that each has a predetermined range of pressure in a pressure increase process of the cuff during the blood pressure measurement,
the programmed processor calculates compliance ratio between each of the cuff compliances calculated during the blood pressure measurement and the reference cuff compliance,
the programmed processor determines whether or not there is external compression on the cuff according to whether or not the compliance ratios are smaller than a predetermined first threshold in a first pressure region in which the pressure of the cuff is 0 mmHg or more and less than 40 mmHg and the compliance ratios are greater than or equal to a predetermined second threshold in a second pressure region in which the pressure of the cuff is 40 mmHg or more and 120 mmHg or less, in the pressure increase process of the cuff, and
the programmed processor operates as a notification unit to output, to the display, compression information that indicates a result of determining whether or not there is external compression in correspondence with the blood pressure value, and the display is controlled by the programmed processor to display the compression information in correspondence with the blood pressure value on a display screen.

5. The electronic blood pressure monitor according to claim 4, further comprising:
a storage unit including a memory and configured to store the compression information in correspondence with the blood pressure value.

* * * * *